(12) United States Patent
Dimmer et al.

(10) Patent No.: US 7,176,798 B2
(45) Date of Patent: *Feb. 13, 2007

(54) SYSTEM FOR SPATIALLY ADJUSTABLE EXCITATION OF LEADLESS MINIATURE MARKER

(75) Inventors: Steven C. Dimmer, Bellevue, WA (US); J. Nelson Wright, Mercer Island, WA (US); William T. Mayo, Seal Beach, CA (US)

(73) Assignee: Calypso Medical Technologies, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/997,080

(22) Filed: Nov. 23, 2004

(65) Prior Publication Data

US 2005/0195084 A1  Sep. 8, 2005

Related U.S. Application Data

(63) Continuation of application No. 10/213,980, filed on Aug. 7, 2002, now Pat. No. 6,822,570, which is a continuation-in-part of application No. 10/044,056, filed on Jan. 11, 2002, now Pat. No. 6,838,990, which is a continuation-in-part of application No. 10/027,675, filed on Dec. 20, 2001, now Pat. No. 6,812,842.

(51) Int. Cl.
  *G08B 13/14* (2006.01)
(52) U.S. Cl. .............................. 340/572.1; 340/572.5; 340/572.7; 343/742
(58) Field of Classification Search ............ 340/572.1, 340/572.4, 572.7, 572.5; 343/742, 867
See application file for complete search history.

(56) References Cited

U.S. PATENT DOCUMENTS

| 3,752,960 A | 8/1973 | Walton |
| 3,967,161 A | 6/1976 | Lichtblau |
| 4,017,858 A | 4/1977 | Kuipers |

(Continued)

FOREIGN PATENT DOCUMENTS

EP  0 719 420  11/1999

(Continued)

OTHER PUBLICATIONS

International Search Report dated Jan. 24, 2003, PCT Application No. PCT/US/29390.

(Continued)

*Primary Examiner*—Thomas Mullen
(74) *Attorney, Agent, or Firm*—Perkins Coie LLP

(57) ABSTRACT

A system for generating a magnetic field for excitation of a leadless marker assembly. The system of at least one embodiment includes a source generator that generates a plurality of alternating electrical signals each having an independently adjustable phase. A plurality of excitation coils are configured to simultaneously receive a respective one of the alternating electrical signals at a selected phase to generate a magnetic field. The phase of the alternating electrical signal for each excitation coil is independently adjustable relative to the phase of the alternating electrical signal for the other excitation coils so as to adjust the magnetic field from the respective coil. The magnetic fields from the excitation coils combine to form a spatially adjustable excitation field for excitation of the remote leadless marker assembly.

31 Claims, 10 Drawing Sheets

U.S. PATENT DOCUMENTS

| | | |
|---|---|---|
| 4,023,167 A | 5/1977 | Wahlstrom |
| 4,123,749 A | 10/1978 | Hartmann et al. |
| 4,160,971 A | 7/1979 | Jones et al. |
| 4,260,990 A | 4/1981 | Lichtblau |
| 4,466,075 A | 8/1984 | Groch |
| 4,633,250 A | 12/1986 | Anderson |
| 4,642,786 A | 2/1987 | Hansen |
| 4,737,794 A | 4/1988 | Jones |
| 4,795,995 A | 1/1989 | Eccleston |
| 4,849,692 A | 7/1989 | Blood |
| 4,945,305 A | 7/1990 | Blood |
| 5,050,608 A | 9/1991 | Watanabe |
| 5,095,224 A | 3/1992 | Renger |
| 5,099,845 A | 3/1992 | Besz |
| 5,142,292 A | 8/1992 | Chang |
| 5,188,368 A | 2/1993 | Ryan |
| 5,198,877 A | 3/1993 | Schulz |
| 5,221,269 A | 6/1993 | Miller |
| 5,240,011 A | 8/1993 | Assa |
| 5,325,873 A | 7/1994 | Hirschi |
| 5,377,678 A | 1/1995 | Dumoulin |
| 5,397,329 A | 3/1995 | Allen |
| 5,411,026 A | 5/1995 | Carol |
| 5,417,210 A | 5/1995 | Funda |
| 5,425,382 A | 6/1995 | Golden |
| 5,446,548 A | 8/1995 | Gerig |
| 5,453,686 A | 9/1995 | Anderson |
| 5,515,853 A | 5/1996 | Smith |
| 5,526,812 A | 6/1996 | Dumoulin |
| 5,528,651 A | 6/1996 | Leksell |
| 5,546,951 A | 8/1996 | Ben-Haim |
| 5,558,091 A | 9/1996 | Acker |
| 5,568,809 A | 10/1996 | Ben-Haim |
| 5,572,999 A | 11/1996 | Funda |
| 5,617,857 A | 4/1997 | Chader |
| 5,622,170 A | 4/1997 | Schulz |
| 5,622,187 A | 4/1997 | Carol |
| 5,629,967 A | 5/1997 | Leksell |
| 5,630,431 A | 5/1997 | Taylor |
| 5,645,065 A | 7/1997 | Shapiro |
| 5,680,106 A | 10/1997 | Schrott |
| 5,681,326 A | 10/1997 | Lax |
| 5,727,552 A | 3/1998 | Ryan |
| 5,745,545 A | 4/1998 | Hughes |
| RE35,816 E | 6/1998 | Schulz |
| 5,764,052 A | 6/1998 | Renger |
| 5,779,638 A | 7/1998 | Vesely |
| 5,797,849 A | 8/1998 | Vesely |
| 5,805,661 A | 9/1998 | Leksell |
| 5,815,076 A | 9/1998 | Herring |
| 5,817,022 A | 10/1998 | Vesely |
| 5,820,553 A | 10/1998 | Hughes |
| 5,823,192 A | 10/1998 | Kalend |
| 5,828,770 A | 10/1998 | Leis |
| 5,830,144 A | 11/1998 | Vesely |
| 5,868,673 A | 2/1999 | Vesely |
| 5,868,675 A | 2/1999 | Henrion |
| 5,879,357 A | 3/1999 | Heaton |
| 5,902,238 A | 5/1999 | Golden |
| 5,902,310 A | 5/1999 | Foerster |
| 5,913,820 A | 6/1999 | Bladen |
| 5,923,417 A | 7/1999 | Leis |
| 5,987,349 A | 11/1999 | Schulz |
| 6,015,390 A | 1/2000 | Krag |
| 6,019,725 A | 2/2000 | Vesely |
| 6,026,818 A | 2/2000 | Blair |
| 6,049,587 A | 4/2000 | Leksell |
| 6,052,477 A | 4/2000 | Wang |
| 6,061,644 A | 5/2000 | Leis |
| 6,064,904 A | 5/2000 | Yanof |
| 6,067,465 A | 5/2000 | Foo |
| 6,094,007 A | 7/2000 | Faul |
| 6,097,994 A | 8/2000 | Navab |
| 6,144,875 A | 11/2000 | Schweikard |
| 6,173,715 B1 | 1/2001 | Sinanan |
| 6,198,963 B1 | 3/2001 | Haim |
| 6,239,724 B1 | 5/2001 | Doron |
| 6,363,940 B1 | 4/2002 | Krag |
| 6,371,379 B1 | 4/2002 | Dames |
| 6,401,722 B1 | 6/2002 | Krag |
| 6,474,341 B1 | 11/2002 | Hunter |
| 2003/0052785 A1 | 3/2003 | Gisselberg |
| 2003/0088178 A1 | 5/2003 | Owens et al. |

FOREIGN PATENT DOCUMENTS

| | | |
|---|---|---|
| EP | 1 034 738 | 9/2000 |
| WO | WO-88/08282 | 11/1988 |
| WO | WO-95/33519 | 12/1995 |
| WO | WO-96/08208 | 3/1996 |
| WO | WO-96/08999 | 3/1996 |
| WO | WO-97/36192 | 10/1997 |
| WO | WO-97/48438 | 12/1997 |
| WO | WO-98/30166 | 7/1998 |
| WO | WO-99/17133 | 4/1999 |
| WO | WO-99/27839 | 6/1999 |
| WO | WO-99/30182 | 6/1999 |
| WO | WO-99/35966 | 7/1999 |
| WO | WO-99/58055 | 11/1999 |
| WO | WO-99/58065 | 11/1999 |
| WO | WO-00/24332 | 5/2000 |
| WO | WO-00/51514 | 9/2000 |
| WO | WO-01/34049 | 5/2001 |
| WO | WO-01/54765 | 8/2001 |
| WO | WO-02/19908 | 3/2002 |
| WO | WO-02/100485 | 12/2002 |

OTHER PUBLICATIONS

Hsiao, K., "Fast Multi-Axis Tracking of Magnetically-Resonant Passive Tags: Methods and Applications," Feb. 2001, Massachusetts Institute of Technology, Dept. of Electrical Engineering and Computer Science.

COMBINED SOURCE AND MARKER SIGNAL
← MEASURED AT SENSORS WHEN MARKER SIGNAL IS →
AT STEADY STATE CONDITION

SYSTEM FOR SPATIALLY ADJUSTABLE EXCITATION OF LEADLESS MINIATURE MARKER

CROSS REFERENCE TO RELATED APPLICATIONS

This application is a continuation of U.S. patent application Ser. No. 10/213,980, titled SYSTEM FOR SPATIALLY ADJUSTABLE EXCITATION OF LEADLESS MINIATURE MARKER, filed Aug. 7, 2002, which issued on Nov. 23, 2004 as U.S. Pat. No. 6,822,570, which is a continuation-in-part of U.S. application Ser. No. 10/044,056, tilted SYSTEM FOR EXCITATION LEADLESS MINIATURE MARKER, filed Jan. 11, 2002, which issued on Jan. 4, 2005 as U.S. Pat. No. 6,838,990, which is a continuation-in-part of U.S. patent application Ser. No. 10/027,675, titled SYSTEM FOR EXCITATION OF LEADLESS MINIATURE MARKER, filed Dec. 20, 2001, which issued on Nov. 2, 2004 as U.S. Pat. No. 6,812,842.

TECHNICAL FIELD

This invention relates to systems for activating miniature markers, and more particularly to systems for excitation of resonating miniature marker assemblies for use in locating the markers in three-dimensional space.

BACKGROUND OF THE INVENTION

Systems have been developed to activate and detect remote activatable marker assemblies positioned, as an example, in or on a selected item or object. The markers generate a signal used to detect the presence of the marker. Many of the activatable markers are hard-wired to a power source or other equipment external from the object. Other systems have been developed that utilize resonating leadless markers, also referred to as wireless active markers, positionable at or near a selected target. These wireless active markers are typically activated or energized by a remote excitation source that generates a strong continuous excitation signal. Accordingly, the markers generate a detectable marker signal that must be distinguished from the strong continuous excitation signal and then analyzed in an effort to try to accurately determine the target's location. The process of distinguishing a weak marker signal from the strong continuous excitation signal, while maintaining sufficient accuracy and repeatability for determining the marker's location, has proven to be very difficult.

Other systems have provided detection of leadless markers to determine a two-dimensional proximity (e.g., X, Y coordinates) to detectors for use with game boards, surgical tag detection devices, and medical tube placement verification systems. In the case of the game boards, a unique game piece with a resonator of a predetermined frequency is moved across the game board, and the X and Y location coordinates of the game piece relative to the game board are displayed so the players can determine the general location of the game piece on the game board. U.S. Pat. No. 5,853,327 to Gilboa identifies that the X, Y coordinates, as a function of amplitude or phase, may be determined experimentally for a given game board design. Additionally, Z distance away from the game board may be determined to a sufficient accuracy for game use by the strength of the signal above the game board provided that the signal is not a strong function of the X and Y locations. U.S. Pat. No. 5,188,368 to Ryan provides a system for determining in two dimensions which individual square of a chess board a particular chess piece is on during a chess game. The system disclosed by Ryan does not determine the Z direction.

In the case of the surgical tag and detection device, U.S. Pat. No. 6,026,818 to Blair discloses surgical devices, such as sponges, that have activatable resonator tags thereon for proximity detection by a hand-held probe. The probe has a single loop interrogation ring provided that can transmit an excitation signal to activate the resonator tag and then be switched to a receiver mode. The probe is moved manually to change the angular orientation of the interrogation ring, thereby moving the resulting excitation field's orientation. The excitation field is moved to a suitable orientation so as to excite resonator tags in various spatial orientations. The interrogation ring can then be scanned over an area of a patient after surgery to determine if any surgical devices having the resonator tags have been left behind. Accordingly, the detection device of Blair is detecting the existence or proximity of a surgical tag with the interrogation ring, rather than the actual location of the activatable tags.

In the case of the medical tube placement verification device, U.S. Pat. No. 5,325,873 to Hirschi et al. teaches a system that detects the general position of an object within a body of tissue. The detection system includes a three-axis resonant-circuit target attached to the object and a separate hand-held detection probe having a pair of parallel and coaxially aligned transmitter/sensing coils. The transmitter sensing coils generate a current that determines whether a return signal strength of the target is great enough to be counted as a valid signal. The hand-held detection probe also has a pair of receiver coils positioned within each of the transmitter coils and connected in a series-opposed fashion. The four receiver coils allow for the creation of a null circuit condition when the target is equidistant from each of the receiver coils. The detection probe also has a visual display coupled to the receiver coils and configured to indicate the direction (e.g., left/right/up/down) in which the probe should be moved to center the detection probe over the object, thereby achieving the null circuit condition.

The systems of the above patents activate the markers with a pulsed excitation signal generated by driving an untuned source coil with either a unipolar polarity to produce a wide band impulse function or a bipolar polarity to create a waveform that more closely matches the desired resonant frequency of the marker. The required levels of magnetic excitation for the markers in the above patents are relatively low such that the excitation energy in the source coil is substantially consumed after each pulse due to the pulse circuitry resistive losses. The source coils are driven by linear amplifiers, and in one case by linear amplifiers at both ends of the coil, and by a simple pulse network that energizes the coil and extinguishes resistively. The amplitude of the pulsed excitation signal required for these applications is relatively low since either the resonator circuit to be located is of a large size, the volume in which the resonator must be located is relatively small, or the accuracy requirements locating the resonator are quite low. Accordingly, the existing systems are not suitable for use in many situations wherein highly accurate determinations of the marker's location in three-dimensional space is required. The existing systems may also not be suitable for use with efficient, high energy systems for energizing the marker assemblies so as to provide a sufficient marker signal for use in determining the location of the marker in three-dimensional space relative to remote sensors.

Other systems have been developed for tracking wireless tags for use as a tangible interface to interact with a computer. Such systems are described in "Fast Multi-Axis Tracking of Magnetically Resonant Passive Tags: Methods and Applications," Kai-yuh Hsiao, Massachusetts Institute of Technology, 2001. As an example, one tracking system utilized wireless markers tracked in three-dimensional space by a single transmitter coil or by aligned multiple coils in a Hemholtz configuration. The multiple coils are continuously swept through a range of frequencies to activate the magnetically resonant passive tags, and the transmitter coils are simultaneously monitored so as to detect and determine the location of the magnetically resonant passive tags.

Other systems have been developed for proximity detection of resonator tags for Electronic Article Surveillance (EAS) systems. The requirements for EAS systems are to detect the presence of a security tag within a six-foot wide aisle using one antenna assembly for both excitation and detection of the tag within the aisle. Some EAS systems utilize tuned resonant excitation source coil drive circuitry for pulsed resonator tag operation. As an example, U.S. Pat. No. 5,239,696 to Balch et al. discloses a linear amplifier using current feedback linear power amplifiers to drive an excitation source tuned to resonant coils for use in pulsed EAS systems. The current feedback is used to adjust the linear amplifier's drive current level provided to the tuned excitation source coil load. The current feedback is also used to provide for a relatively constant current drive for exciting resonant EAS tags in the field. The source coil is tuned to allow for use of a simple, low voltage linear amplifier circuit design. The source coil current pulse waveform is determined by the summation of the sinusoidal control signal and the drive current feedback signal input to the linear amplifier.

U.S. Pat. No. 5,640,693 to Balch et al. discloses the use of linear power amplifiers to drive excitation source coils for use in pulsed EAS systems. An apparatus for switching power to a linear amplifier is provided to turn to an "on" state and an "off" state used to control the output drive pulse burst of the tuned excitation source coils. Balch et al. '693 also identifies that linear amplifiers which generate drive signals for a source coil since linear amplifiers are typically only about thirty to forty percent efficient. The inherent inefficiency of the linear amplifier drive is improved by switching the amplifier power "on" and "off" at the same time that the pulse control input signal to the power supply is switched to an "on" and "off" position.

U.S. Pat. No. 5,815,076 to Herring teaches one or more damping circuits provided in series with excitation source coils and used to promote rapid dampening of the pulsed excitation interrogation signals at the end of each signal pulse. Providing the switchable damping circuits in series with the antennas increases the power dissipation of the device during pulse delivery due to added damping circuit switch resistance in the antenna current path.

The above systems employ a resonator circuit energized with an excitation signal and the resonator response signal is measured with sensing coils. The amplitude of the pulsed excitation signal required for these applications is relatively low since either the resonator circuit to be located is of a large size, the volume in which the resonator must be located is relatively small, or the accuracy requirements locating the resonator are quite low.

SUMMARY OF THE INVENTION

Under one aspect of the invention, a system is provided for generating a magnetic field for excitation of a leadless marker assembly. The system of at least one embodiment includes a source generator that generates a plurality of independently controlled, alternating electrical signals each having an adjustable phase relative to each other. A plurality of excitation coils are independently coupled to the source generator, and each excitation coil has a coil axis axially misaligned with the coil axis of the other excitation coils. The excitation coils are configured to simultaneously receive a respective one of the alternating electrical signals at a selected phase to generate a magnetic field. The phase of the alternating electrical signal for each excitation coil is independently adjustable relative to the phase of the alternating electrical signal for the other excitation coils so as to adjust the magnetic field from the respective coil. The magnetic fields from the excitation coils combine to form a spatially adjustable excitation field for excitation of the remote leadless marker assembly.

Another embodiment includes a marker system with a switching network coupled to an energy storage device. A plurality of excitation coils are independently coupled to the switching network. Each of the excitation coils has a coil axis that is non-concentric with the coil axis of the other excitation coils. The excitation coils are configured to simultaneously receive from the switching network alternating electrical signals at a selected phase to generate a magnetic field from the respective coil. The switching network is manipulatable to independently change the phase for each excitation coil. The magnetic fields from the excitation coils are configured to combine with each other to form a modifiable excitation field having selected spatial characteristics for excitation of the leadless marker assembly. The spatially adjustable excitation field of this embodiment effectively avoids blind spots in the excitation of single axis marker assemblies and therefore allows the marker assemblies to be in any orientation relative to the pulsed source generator coil assembly and still be highly energized upon activation of the excitation source coils.

Another embodiment is directed to a marker system with a plurality of leadless resonating marker assemblies excitable by a magnetic excitation signal and being configured to generate marker resonant signals at one or more selected resonant frequencies. The excitation system is programmable and allows for sequential excitation of unique resonant frequency marker assemblies that may be positioned at different orientations relative to the source coil assembly. For example, the excitation system could excite three unique frequency resonators each of which is oriented substantially along one of the three axes (X, Y and Z) by changing the directionality state of the source coil drive before the excitation interval of the resonator of interest and providing excitation signals that are of the appropriate directionality. A plurality of location sensors are remote from the marker assemblies and configured to receive the marker signals. A source generator assembly has an energy storage device, first and second switching networks connected to the energy storage device, and first and second excitation coils. The first and second excitation coils are substantially coplanar. The first switching network and the first excitation coil are interconnected and independent of the second excitation coil. The second switching network and the second excitation coil are interconnected and independent of the first excitation coil.

Another embodiment is directed to a method of energizing a leadless marker assembly. The method includes directing alternating electrical signals via a switching network through a plurality of excitation coils that are axially misaligned relative to each other to generate a plurality of magnetic fields having selected phases so the magnetic fields combine to form a shaped excitation field. The method also includes energizing a leadless resonating marker assembly with the spatially adjustable excitation field.

Another embodiment is directed to another method of energizing a leadless marker assembly. The method includes directing alternating electrical signals having an independently adjustable phase through a plurality of excitation coils to generate a plurality of magnetic fields that combine to form a spatially adjustable excitation field. The method also includes energizing a leadless resonating marker assembly with the spatially adjustable excitation field.

DETAILED DESCRIPTION

In the following description, certain specific details are set forth in order to provide a thorough understanding of various embodiments of the invention. However, one skilled in the art will understand that the invention may be practiced without these details. In other instances, well-known structures associated with magnetic excitation systems, resonating markers, and activators have not been shown or described in detail to avoid unnecessarily obscuring the description of the embodiments of the invention.

FIGS. 1–16 illustrate a system and components for generating an excitation signal for activating a resonating marker assembly and locating the marker in three-dimensional space in accordance with embodiments of the present invention. Several of the components described below with reference to FIGS. 1–16 can also be used in systems for performing methods in accordance with aspects of the present invention. Therefore, like reference numbers refer to like components and features throughout the various figures.

Figure 1:
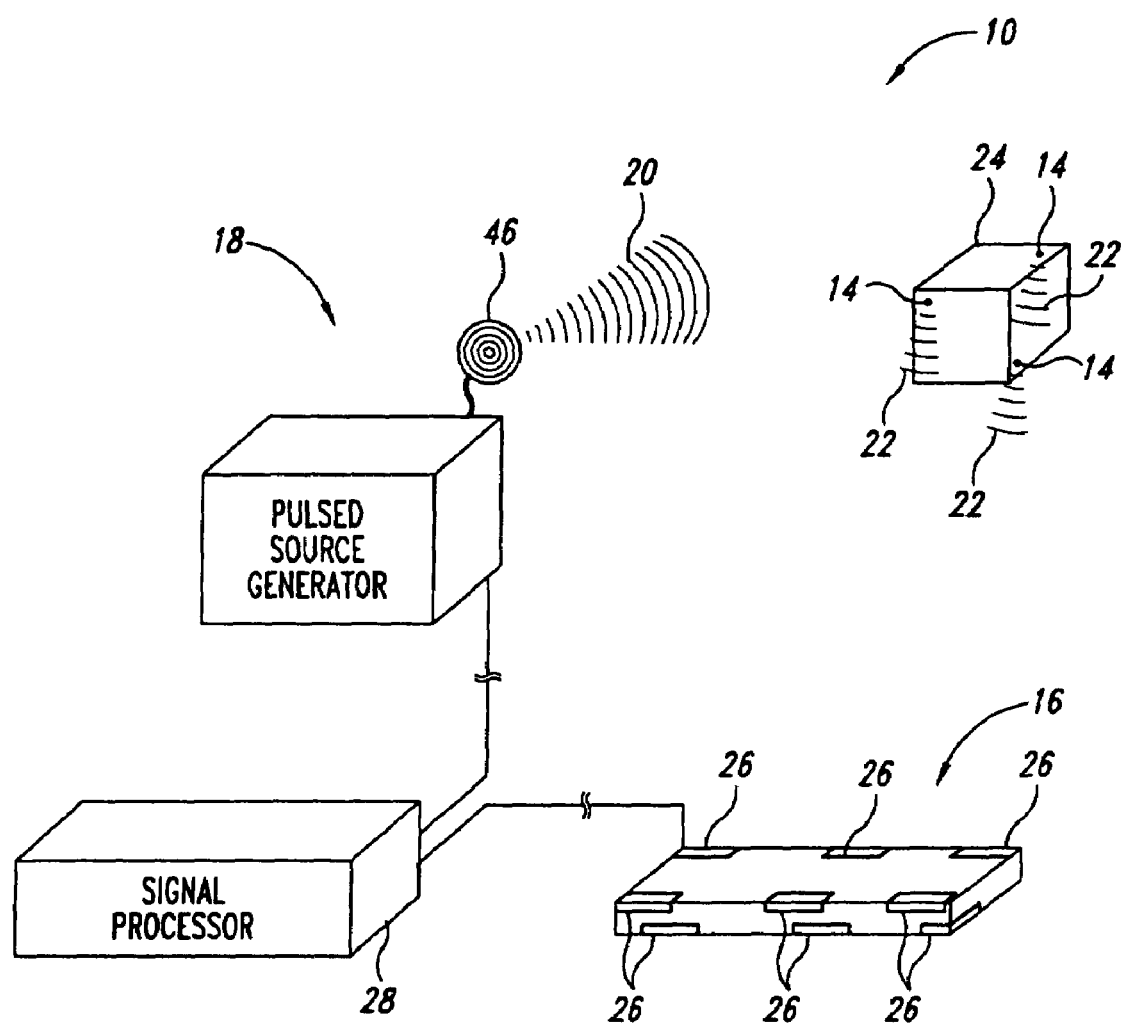
FIG. 1 is a schematic isometric view of a system for energizing and locating leadless miniature markers in accordance with an embodiment of the present invention.
Figure 2:
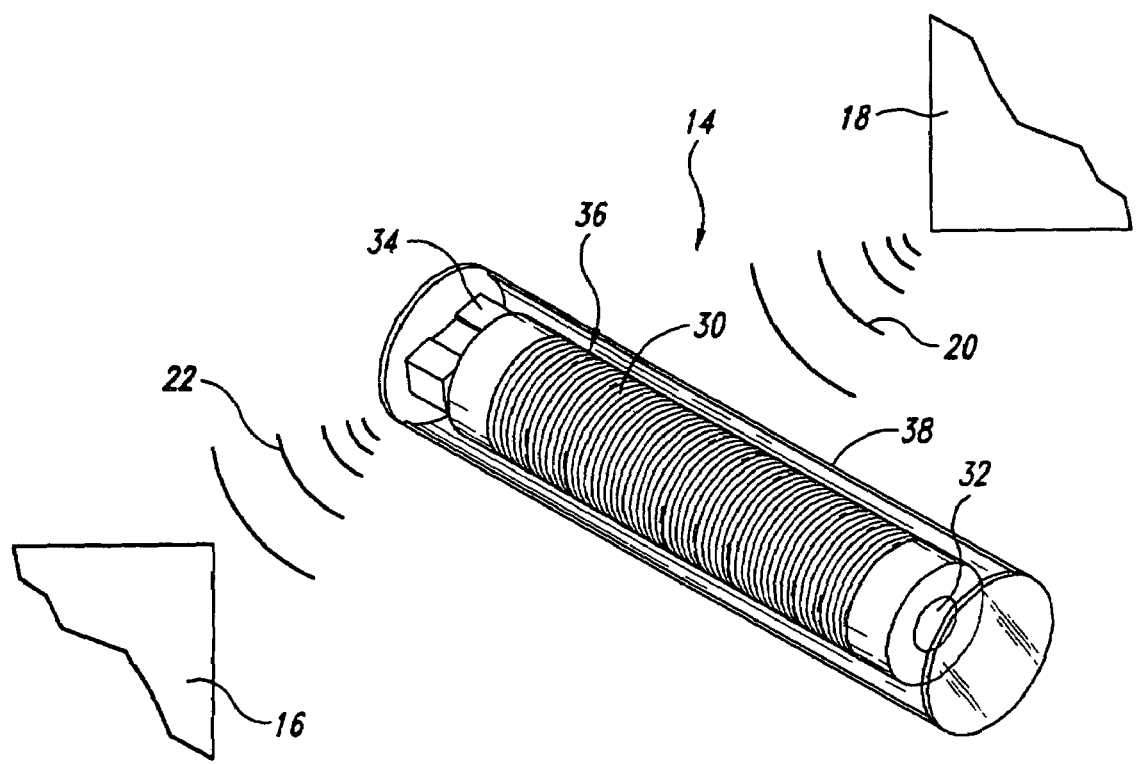
FIG. 2 is an isometric view of an embodiment of an implantable miniature resonating marker assembly usable in the system of FIG. 1.

FIG. 1 is a schematic isometric view of a system 10 for energizing and locating one or more leadless resonating marker assemblies 14 in three-dimensional space relative to a sensor array 16 in accordance with one embodiment of the present invention. The system 10 includes a source generator 18 that generates a selected magnetic excitation field or excitation signal 20 that energizes the marker assemblies 14. The energized marker assemblies 14 generate a measurable marker signal 22 that can be sufficiently measured in the presence of both the excitation source signal and environmental noise sources. In the illustrated embodiment, the marker assemblies 14 are positioned in or on a selected object 24 in a known orientation relative to each other. The marker signals 22 are measured by a plurality of sensors 26 in the sensor array 16. The sensors 26 are coupled to a signal processor 28 that utilizes the measurement of the marker signals 22 from the sensors 26 to calculate the location of each marker assembly 14 in three-dimensional space relative to a known frame of reference, such as the sensor array 16.

In the illustrated embodiment, as discussed in greater detail below, the source generator 18 is configured to generate the excitation signal 20 so that one or more marker assemblies 14 are sufficiently energized to generate the marker signals 22. In one embodiment the source generator 18 can be switched off after the marker assemblies are energized. Once the source generator 18 is switched off, the excitation signal 20 terminates and is not measurable. Accordingly, the sensors 26 in the sensor array 16 will receive only the marker signals 22 without any interference or magnetic field distortion induced by the excitation signal 20. Termination of the excitation signal 20 occurs before a measurement phase in which marker signals 22 are measured. Such termination of the excitation signal before the measurement phase when the energized marker assemblies 14 are generating the marker signals 22 allows for a sensor array 16 of increased sensitivity that can provide data of a high signal-to-noise ratio to the signal processor 28 for extremely accurate determination of the three-dimensional location of the marker assemblies 14 relative to the sensor array or other frame of reference.

The miniature marker assemblies 14 in the system 10 of the illustrated embodiment are inert, activatable assemblies that can be excited to generate a signal at a resonant frequency measurable by the sensor array 16 remote from the target 24. In one embodiment, the miniature marker assemblies 14 have, as one example, a diameter of approximately 2 mm and a length of approximately 5 mm, although other marker assemblies can have different dimensions. An example of the marker detection system is described in detail in co-pending U.S. patent application Ser. No. 09/877,498, titled GUIDED RADIATION THERAPY SYSTEM, filed Jun. 8, 2001, which is incorporated herein in its entirety by reference thereto.

The illustrated marker assembly 14 includes a coil 30 wound around a ferromagnetic core 32 to form an inductor (L). The inductor (L) is connected to a capacitor 34, so as to form a signal element 36. Accordingly, the signal element 36 is an inductor (L) capacitor (C) resonant circuit. The signal element 36 in one embodiment is enclosed and sealed in an encapsulation member 38 made of plastic, glass, or other inert material. The illustrated marker assembly 14 is a fully contained and inert unit that can be used, as an example, in medical procedures in which the marker assembly is secured on and/or implanted in a patient's body.

Other marker assemblies 14 are described in detail in co-pending U.S. patent application Ser. No. 09/954,700, filed Sep. 14, 2001, which is also incorporated herein in its entirety by reference thereto. Other leadless marker assemblies 14 that may be used are described in detail in U.S. Pat. No. 6,363,940, titled SYSTEM AND METHOD FOR BRACKETING AND REMOVING TISSUE, filed May, 14, 1998; PCT Application No. PCT/US00/31667 titled SYSTEMS AND METHODS FOR LOCATING AND DEFINING A TARGET LOCATION WITHIN A HUMAN BODY, filed Nov. 17, 2000; and PCT/US00/31673, titled SYSTEMS AND METHODS FOR STABILIZING A TARGET LOCATION WITHIN A HUMAN BODY, filed Nov. 17, 2000, all of which are incorporated herein in their entireties by reference thereto.

The marker assembly 14 is energized, and thus activated, by the magnetic excitation field or excitation signal 20 generated by the source generator 18 such that the marker's signal element 36 generates the measurable marker signal 22. The strength of the measurable marker signal 22 is high relative to environmental background noise at the marker resonant frequency, thereby allowing the marker assembly 14 to be precisely located in three-dimensional space relative to the sensor array 16.

The source generator 18, in one embodiment, is adjustable to generate a magnetic field 20 having a waveform that contains energy at selected frequencies that substantially match the resonant frequency of the specifically tuned marker assembly 14. When the marker assembly 14 is excited by the magnetic field 20, the signal element 36 generates the response marker signal 22 containing frequency components centered at the marker's resonant frequency. After the marker assembly 14 is energized for a selected time period, the source generator 18 is switched to the "off" position so the pulsed excitation signal 20 is terminated and provides no measurable interference with the marker signal 22 as received by the sensor array 16.

The marker assembly 14 is constructed to provide an appropriately strong and distinct signal by optimizing marker characteristics and by accurately tuning the marker assembly to a predetermined frequency. Accordingly, multiple uniquely tuned, energized marker assemblies 14 may be reliably and uniquely measured by the sensor array 16. The unique marker assemblies 14 at unique resonant frequencies may be excited and measured simultaneously or during unique time periods. The signal from the tuned miniature marker assembly 14 is significantly above environmental signal noise and sufficiently strong to allow the signal processor 28 (FIG. 1) to determine the marker assembly's identity, precise location, and orientation in three dimensional space relative to the sensor array 16 or other selected reference frame.

The system 10 of the illustrated embodiment in FIG. 1 can be used in many different applications in which the miniature marker's precise three-dimensional location within an accuracy of approximately 1 mm can be uniquely identified within a relatively large navigational or excitation volume, such as a volume of 12 cm×12 cm×12 cm or greater. One such application is the use of the system 10 to accurately track the position of targets (e.g., tissue) within the human body. In this application, the leadless marker assemblies 14 are implanted at or near the target so the marker assemblies move with the target as a unit and provide positional references of the target relative to a reference frame outside of the body. Such a system could also track relative positions of therapeutic devices (i.e., surgical tools, tissue ablation devices, radiation delivery devices, or other medical devices) relative to the same fixed reference frame by positioning additional leadless marker assemblies 14 on these devices at known locations or by positioning these devices relative to the reference frame. The size of the leadless markers used on therapeutic devices may be increased to allow for greater marker signal levels and a corresponding increase in navigational volume for these devices.

The system 10 is configured to generate a sufficient source excitation magnetic field signal, as an example, source excitation coil Magnetic Dipole Moment approximately greater than 0.5 A*m$^2$, at the appropriate frequency to energize the one or more marker assemblies significantly above the environmental background noise. In one embodiment, the system 10 also generates excitation source magnetic field flux signals at selected spatial orientations (e.g., so the magnetic moment is substantially oriented along the X, Y and Z axes). The magnetic field flux signals excite a marker assembly 14 that may be a resonator having a single coil (i.e., a single-axis coil) substantially oriented along a single axis and spatially orthogonal to excitation energy along the other two axes. The system 10 can also be configured to generate excitation source magnetic field flux signals at variable frequencies to energize a plurality or marker assemblies 14 that contain resonant circuits tuned to these unique frequencies. Accordingly, the multiple marker assemblies 14 can be sequentially or simultaneously energized.

The system 10 is also configured to avoid the difficult process of separating the small marker signal 22 from the much more powerful source excitation signal 20 by measuring the marker signal during a time period when the source signal is substantially not present. The residual source excitation signal 20 can cause substantially less accurate results in the location determination if not controlled. The system 10 provides for the measurement of the marker signal 22 with a sufficient number of spatially distributed sensors 26 at a sufficient signal-to-noise ratio so that an inversion algorithm provided in the signal processor 28 can accurately solve for the three-dimensional location of the particular marker assembly 14 relative to the known reference frame of the sensor array 16.

Figure 3:
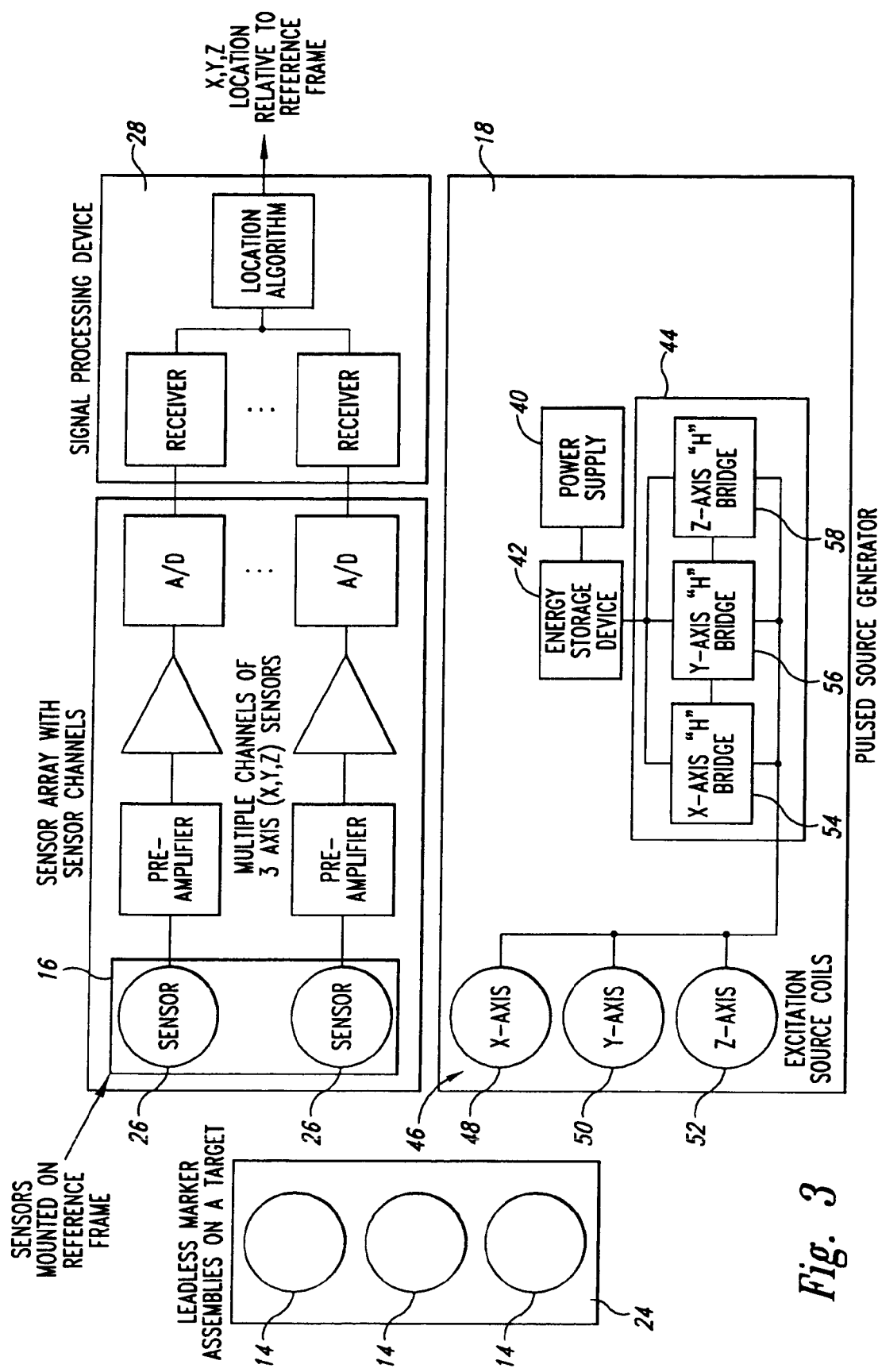
FIG. 3 is a schematic block diagram of the excitation system of FIG. 1 illustrating a source signal generator, a signal processing device, a sensor array, and leadless markers.

FIG. 3 is a schematic block diagram of the system 10 in accordance with one embodiment. As seen in FIG. 3, the plurality of leadless miniature marker assemblies 14 on the target 24 are remote from the source generator 18 and from the sensor array 16. The sensor array 16 is operatively coupled to the signal processing device 28.

The source generator 18 includes a high voltage power supply 40 coupled to an energy storage device 42. In one embodiment, the power supply 40 is a 500 volt power supply, although other power supplies with higher or lower voltages can be used. The energy storage device 42 in one embodiment is a high voltage capacitor that can be charged and maintained at a relatively constant charge by the power supply 40. Energy stored in the storage device 42 allows for providing energy to and removing energy from the source coil inductor. A small amount of stored energy is present in the source coil inductor at maximum current relative to the energy stored in the energy storage device 42.

The energy storage device 42 is capable of storing adequate energy to minimize voltage droop in the energy storage device while having a low series resistance so as to minimize power losses. The energy storage device 42 also has a low series inductance to allow for maximum source generator excitation capability to drive the source coil 46. Specialized aluminum electrolytic capacitors used in flash energy applications may be used in one of the embodiments of system 10. Alternative energy storage devices can also include NiCd and lead acid batteries, as well as alternative capacitor types, such as tantalum, film, or the like.

The source generator 18 of the illustrated embodiment also includes a switching network 44 coupled between the energy storage device 42 and a plurality of untuned excitation source coils 46. The switching network 44 is configured to control the polarity of the voltage across the source coils 46 and the resultant current magnitude and polarity with time through the source coils so that the source coils 46 each generate the high energy excitation field 20 for activating the marker assemblies (FIG. 1).

In the illustrated embodiment, the excitation source coils 46 includes three coils orthogonally oriented to correspond to the X, Y, and Z axes of a selected frame of reference. The three coils will be referred to herein as the X coil 48, Y coil 50, and Z coil 52, each of which is configured to provide a magnetic field flux signal along the respective X, Y, and Z axes. The X, Y, and Z coils 48, 50, and 52 with their orthogonal orientation effectively avoid blind spots for excitation of marker assemblies 14 and can allow the marker assemblies to be in any orientation relative to the source generator 18 and still be highly energized upon activation of the excitation source coils 46.

The source coil 46 in the illustrated embodiment is configured to deliver adequate source excitation magnetic fields, which is defined by the area, number of turns, current, and other characteristics of the coil. The source coil 46 is constructed with conductors designed to minimize power loss due to resistive losses as well as resistive losses due to skin effects. Examples include small diameter wire wound in a LITZ wire configuration to minimize skin effects, or alternatively, a thin sheet of conductor to minimize skin effects. Parasitic interwinding capacitance of the source coil inductor and interconnection conductors should also be minimized to reduce unintended coil current spikes due to very short switching network voltage transition times and other unintended source coil resonant circuit affects.

The switching network 44 in the illustrated embodiment includes a plurality of switches that control energy flow to the X, Y, and Z coils 48, 50 and 52. These switches include X-switches 54 coupled to the X-coil 48, Y-switches 56 coupled to the Y-coil 50, and Z-switches 58 coupled to the Z-coil 52. The X-switches 54 include a plurality of activatable switch mechanisms that control the polarity of the voltage across the X coil 48 so as to control the polarity of the derivative with time of the current flow through the X coil. The Y switches 56 control the polarity of the voltage across the Y coil 50 so as to control the polarity of the derivative with time of the current flow through the Y coil. Similarly, the Z-switches 58 are configured to control the polarity of the voltage across the Z coil 52 so as to control the derivative with time of the current flow through the Z coil. The derivative with time of the current flow at a particular voltage polarity across a particular source coil results in either an increasing or decreasing current ramp with time through the source coil.

In the illustrated embodiment, each of the X, Y, and Z switches 54, 56, and 58 have an H-bridge configuration with four switch mechanisms controlled to selectively direct electrical current through the respective X, Y, or Z coil 48, 50, and 52, thereby generating a pulsed magnetic field from the respective source coil.

The X, Y, and Z switches 54, 56, and 58 are also each configured to alternately switch between first and second "on" positions to generate a current flow with a bipolar waveform. In the first "on" position, the current flow in one has a continually increasing current ramp with time through the respective X, Y, or Z coil 48, 50 or 52 to generate the magnetic excitation field. In the second "on" position, the current flow has a continually decreasing current ramp with time through the respective X, Y, or Z coil 48, 50 or 52 to generate the magnetic excitation field. Such alternate switching over the pulse waveform period effectively provides for alternating the polarity of the current flow from a positive polarity to a negative polarity. The X, Y, and Z switches 54, 56, and 58 are also configured to alternately transfer stored energy from the energy storage device 42 to the respective X, Y, or Z axis source coil 48, 50, or 52 and to transfer the stored energy from the respective source coil back to the energy storage device when alternately switching between the first and second "on" positions.

The X, Y, and Z switches 54, 56, and 58 in one embodiment are also configured to move to an "off" position to prevent energy transfer from the energy storage device 42 to the respective X, Y, or Z coils 48, 50, or 52. Once the X, Y, or Z switch 54, 56, or 58 is switched to the "off" position at the appropriate time when the energy (i.e. the current) in the source coil is substantially zero, the respective X, Y, or Z coil 48, 50, or 52 no longer generates a magnetic field such that the pulsed excitation signal 20 ceases, so only the marker signal 22 emanating from the marker assembly 14 is measurable.

Figure 4:
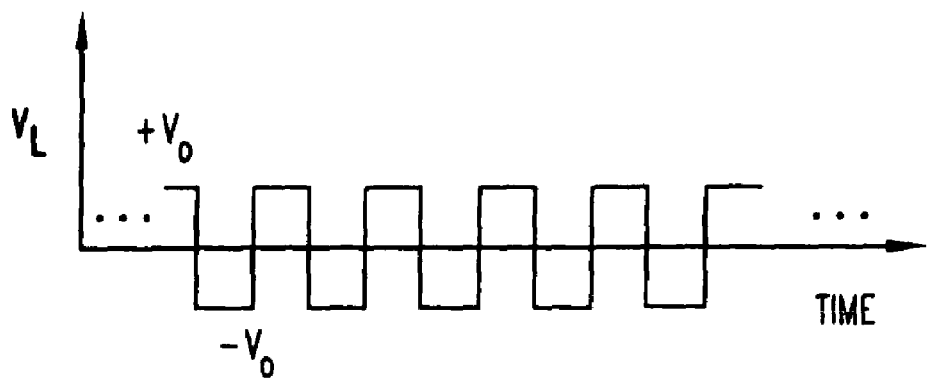
FIG. 4 is a schematic voltage diagram showing the voltage across a source coil of the system of FIG. 1 during excitation phases over time for the continuous wave (CW) excitation and location of the marker assembly.
Figure 5:
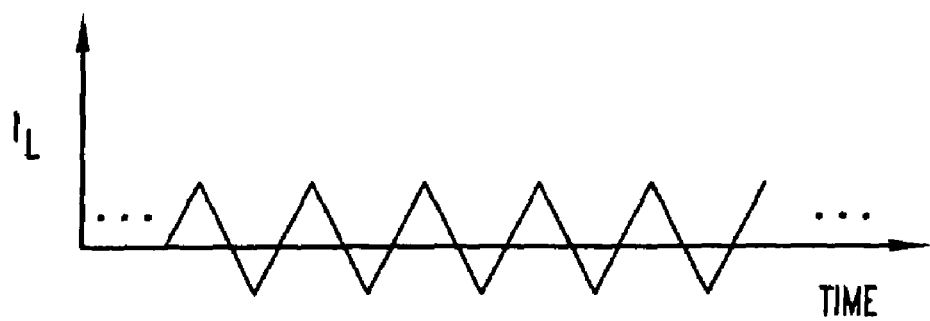
FIG. 5 is a schematic bipolar current diagram during the excitation phase and over time of FIG. 4 for the continuous wave (CW) excitation and location of the marker assembly.

In an alternate embodiment, the source generator 18 is configured to provide a continuous wave excitation signal as the X, Y, and Z switches 54, 56, and 58 alternatively switch between the first and second "on" positions to energize the leadless marker assemblies 14. FIG. 4 illustrates a schematic voltage diagram showing a bipolar voltage across a source coil 64 to generate the continuous excitation signal, and FIG. 5 is a schematic bipolar current diagram of the continuous excitation signal corresponding to the voltage diagram of FIG. 4.

The X, Y, and Z coils 48, 50, and 52 are untuned coils so that the frequency of the excitation signal 20 can be changed or modified to match the different resonant frequencies of a plurality of marker assemblies 14. The frequency of the excitation signal 20 can be changed after the marker assembly 14 is energized. The sensor array 16 and the signal processor 28 can distinguish the marker signal 22 from the excitation signal 20 by measuring the marker resonant signal while the source signal is substantially present but of a different frequency from the measured marker frequency.

Accordingly, the source signal generator excitation waveform is substantially present during measurement of the leadless marker signal 22.

The use of a highly energy efficient source generator 18 that drives an untuned source coil allows for dynamic adjustment of source coil's continuous waveform excitation signal frequency without adjusting or modifying the tuning capacitor of a tuned resonant source coil circuit. This feature allows for adjustment of the source coil's continuous waveform excitation signal frequency to excite multiple uniquely tuned marker resonators during different time periods from the same source coil without modifying a source coil tuning capacitance that is present in a tuned source coil embodiment. Furthermore, an untuned source coil embodiment is not susceptible to source detuning effects of tuned source coil embodiments.

In another embodiment, the source frequency may be adjusted such that the marker signal 22 is a lagging 90 degrees phase difference with the excitation signal 20 when the marker assembly 14 is excited at the resonant frequency of the marker assembly. Accordingly, the signal can be distinguished from the marker signal because of the phase difference between the source and one or more marker signals.

Therefore, different embodiments of the invention may distinguish the marker signal from the source signal because of time, phase or frequency differences between the source and one or more marker signals.

The alternating current flow through the X, Y, or Z coil 48, 50, or 52 generates the pulsed magnetic field in the selected axis to excite the marker assembly 14 located at a determinable distance from the coil. The following is an equation for calculation of the on-axis magnetic field excitation at a distance from a source coil Inductor of a solenoid shape:

$$B_{marker}(\text{distance}) = \frac{\mu_o \cdot I_{source} \cdot r_{source}^2 \cdot N_{source}}{2 \cdot (r_{source}^2 + \text{Distance}^2)^{\frac{3}{2}}}$$

Where:

$B_{marker}$(distance)=magnetic field flux density at a distance from the source coil along the coil axis $\mu_o$=permeability of free space between the source coil and the marker assembly $r_{source}$=Radius of the source coil (meters)

$N_{source}$=Number of turns of wire around the source coil

Distance=distance from the source coil (meters)

$I_{source}$=Electrical current through source coil (amperes)

The electrical current ($I_{source}$) through the X, Y, or Z coil 48, 50, or 52 is determined by the voltage applied across the coil inductance (L). The inductance (L) of an air core coil (solenoid) is approximated by:

$$L = \frac{(\mu_o \cdot \pi \cdot r_{source}^2 \cdot N_{source}^2)}{length_{source}}$$

Where:

L=Inductance of the source coil $\mu_o$=permeability of free space $r_{source}$=Radius of the source coil (meters)

$N_{source}$=Number of turns of wire around the source coil $length_{source}$=Length of source coil (meters)

The inductance of the source coil determines the electrical current derivative with time through source coil inductor as follows:

$$V = L*dI/dt \text{ or } V/L = dI/dt$$

Where:

V=voltage potential across the coil (volts)

L=Inductance of the source coil dI/dt=The change in coil current with time

To efficiently transfer energy to a coil and create the magnetic excitation field, power losses due to resistance in the source coil circuit should be minimized. The power (i.e., RMS power) in the system is determined as follows:

$$P = I^2 R_{TOTAL}$$

Where:

I=Root Mean Square value of the current $R_{TOTAL}$=Total resistance in the source coil circuit The power losses of the system 10 limits the strength of the magnetic excitation field that the system is capable of delivering. When the marker excitation distance is large compared to the effective radius of the magnetic field source, the strength of the magnetic excitation field decreases with the cube the distance from the magnetic field source (e.g., the source coil 46). When the marker excitation distance is not large compared to the effective radius of the magnetic field source, the strength of the magnetic excitation field decreases much less rapidly with the distance from the magnetic field source (e.g., the source coil 46). Furthermore, the magnetic excitation field increases linearly with current, but the power dissipation in the system increases as the square of the current. Accordingly, the requirements for source drive electronics become more challenging to allow for adequate levels of the marker signal 22 as the magnetic excitation field requirements increase.

In one embodiment, the source coil 46 can be operated as a tuned circuit wherein the source coil inductor is tuned with a capacitor chosen for the desired resonant frequency of the marker assembly 14. The reactance of the inductor is equal to and opposite the capacitor at the frequency of interest, such that only the resistance of the source coil circuit is seen by the drive electronics. Substantial stored energy can occur in the tuned circuit, however, that may limit the time in which the source coil excitation signal is shutoff. Longer shut-off time reduces the time during which the marker resonator signal can be measured effectively in the absence of the source signal. Accordingly, a shorter shutoff time can be very desirable. A shorter shutoff time also allows for adequate marker ring down signal to remain after the source signal has decayed such that the marker signal may be measured at a sufficient signal to noise ratio for accurate location of the marker.

The system 10 of the one embodiment provides an untuned source coil 46 configured to excite the leadless marker assembly's resonator with the pulsed excitation signal 20 having a high level of source excitation energy. The system 10 also provides a very short source excitation turnoff time to achieve optimal performance for measuring the marker signal 22 after the source excitation signal 20 is significantly extinguished. Accordingly, the turnoff time for an untuned source coil can have a significant impact on the effectiveness of the system 10, so the system is configured to have only limited stored energy after turnoff time. Therefore, the source generator 18 of the system 10 is configured to deliver high source coil current amplitudes at the optimal marker excitation frequencies to energize the leadless markers 14 before the time decaying marker ring down signal is measured.

Figure 6:
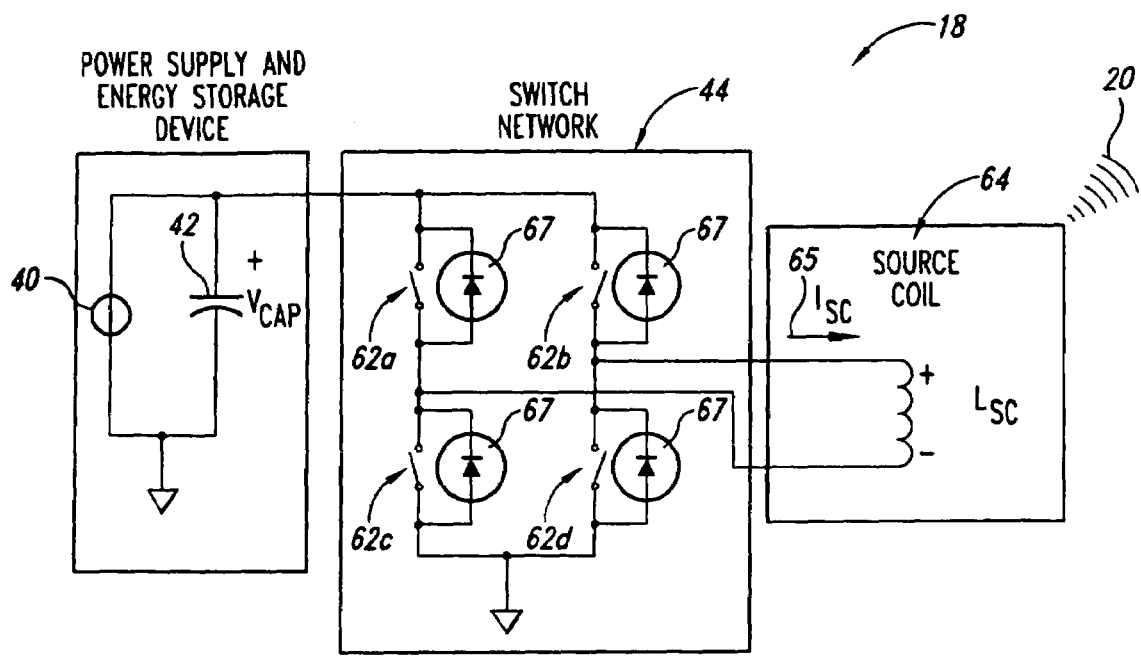
FIG. 6 is a schematic block diagram of an embodiment of the source signal generator of FIG. 3.

FIG. 6 is a schematic block diagram of a source generator 18 of one embodiment. In this illustrated embodiment, a high-voltage power supply 40 and energy storage device 42 are shown coupled to a single switch network 44, which has a single H-bridge switching configuration. This switch network 44 has four switches 62a–d coupled together so as to control the current flow to a single source coil 64. In this embodiment, when multiple source coils are used, each source coil is coupled to a separate switch network 44, power supply 40, and energy storage device 42. In one embodiment, a common energy storage device 42 and a common power supply 40 for multiple switching networks 44 and corresponding source coils are used, as shown in FIG. 3.

The switch network 44 of the illustrated embodiment with the H-bridge configuration is constructed of MOSFET devices. The switching devices have a low "on" series of resistance (less than or equal to approximately 1 ohm) to minimize power losses. Furthermore, very short switching times (less than approximately 25 nanoseconds) are provided to minimize switching induced power losses and maximum excitation delivery. The short switching times allow for high frequency system operation (for example, 50–600 kHz) that improves overall system performance due to increases in inductive coupling efficiencies between the source, marker, and sensor coils with frequency. Alternate embodiments have switch networks 44 that include one-half H-bridge configurations (having only two switches) with a matched set of power supplies and two matched energy storage devices configured to deliver a bipolar voltage drive to the source coil 46. The alternative switching components can include bipolar junction transistors (BJT), JFETs, and various possible vacuum tube configurations.

The power supply 40 directs charge to and maintains a relatively constant energy storage level at the energy storage device 42 by delivering average power to the energy storage device. The amplitude of the charging current is large enough to compensate for average power consumption in the pulse generator and keep the energy storage device at a relatively constant voltage. The energy storage capacitor must be large enough to minimize voltage droop during pulse generation and capable of both supplying high instantaneous power to the switch network and returning high instantaneous power from the switch network 44. The following example for one embodiment has equations for both calculation of the power supply average power and pulse generator instantaneous power delivery:

| | |
|---|---|
| $V_{cap}$ = 500 V | Capacitor charge voltage |
| $R_{switching}$ = 2.0 ohm | Total resistance in "on" state (2 switches closed at a time) |
| $R_{coil}$ = 0.25 ohm | Source coil resistance |
| $R_{energy\_storage\_device}$ = 0.05 ohm | Energy storage device resistance |
| $I_L$(rms) = 4.8 amps | Source coil rms current (during pulsing) |
| Duty cycle = 50% | % of time generator is pulsing |
| Average power dissipation = | $(R_{switching} + R_{coil} + R_{energy\_storage\_device}) * I_L(rms)^2 *$ Duty cycle |
| $P_{Power\_supply}$ (average) = | $(2 + 0.25 + 0.05) * (4.8)^2 * 0.5$ Watts |

| | |
|---|---|
| $P_{Power\_supply}$ (average) = | 26 watts |
| $P_{instantaneous}$ (during pulsing) = | 500 V * 4.8 amps RMS = 2,400 VA RMS |

To maintain constant energy storage:

$I_{Power\_supply}$(average)=$P_{Power\_supply}$(average)/$V_{cap}$ $I_{Power\_supply}$(average)=26 $W$/500$V$=52 milli Ampere The switch network 44 is configured so pairs of the switches 62a–d are opened and closed simultaneously when the other pair of switches are simultaneously closed and opened. As a result, the switch network 44 is configured to control the voltage across the source coil 64 in alternating polarities and at selected phases relative to each other. As a result, the current flow through the source coil 64 alternates between positive and negative polarity over the pulsed magnetic excitation signal waveform pulse burst time period. This alternating of the current flow through the source coil between positive and negative polarity results in the pulsed magnetic excitation signal 20 from the source coil.

In one embodiment, the switch network 44 moves between the first "on" position when switches 62b and 62c are closed and switches 62a and 62d are open, and the second "on" position when switches 62b and 62c are open and switches 62a and 62d are closed. In this first "on" position, the voltage having a positive direction across the source coil 64 increases the current over the pulse "on" time through the source coil in the direction of arrow 65. In the second "on" position, the voltage having a negative direction across the source coil 64 decreases the current over the pulse "on" time through the source coil in the opposite direction of arrow 65. The resulting pulsed excitation signal due to multiple pulses over the pulse burst time period and the repetition frequency of the pulse burst has determinable frequency components corresponding to the resonant frequencies of the marker assemblies 14 for activation of the markers (not shown).

The switch network 44 in the one embodiment also includes an "off" position that opens the circuit to prevent the current from flowing to the source coil. Accordingly, no magnetic field is generated and no pulsed excitation signal 20 is emanated from the source coil 64. The switch network 44 can be switched to the "off" position by opening switched 62a and 62b and by turning 62c and 62d to a closed position to shunt the source coil which allows for exponential decay of residual energy in the source coil. The current then circulates through one of the two switches 62c and 62d and one of two H-bridge protection diodes 67 coupled to the switches depending on the polarity of the residual current. The residual current in the source coil decays by the following exponential time constant:

$\tau = L_{sc}/(R_L + R_{switch} + R_{protection\_diode})$ where:
$L_{sc}$=Source coil inductance
$R_L$=Source coil resistance
$R_{switch}$=Switch "on" resistance
$R_{protection\_diode}$=Protection diode "on" resistance As a result, the switch network 44 is controllable to control the excitation signal 20 and can be switched to the "off" position to terminate the excitation signal after the marker assemblies have been sufficiently energized. When the excitation signal is off, the marker signals 22 do not have to be distinguished from the excitation signal 20 when the marker signal is being measured and analyzed as discussed above.

In an alternate embodiment, the switch network 44 can be switched to the "off" position by opening by opening all switches 62a–d. However, care must be taken to assure that little residual energy remains in the source coil 64 at the time all switches are turned "off", otherwise inductive kick back induced voltage spikes due to an instantaneous current change through the inductor with time may damage the switch network or result in undesired oscillations of the residual current in the source coil.

Figure 7:
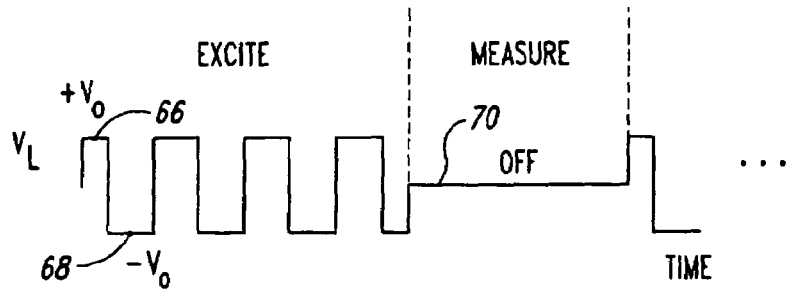
FIG. 7 is a schematic voltage diagram showing the voltage across a source coil of the system of FIG. 1 during excitation "on" and excitation "off" phases over time for the pulsed excitation and location of the marker assembly.

FIG. 7 is a schematic voltage diagram showing the bipolar voltage across a source coil 64 to generate the pulsed excitation signal. The voltage is controlled by activating the switch network 44, as discussed above with respect to FIG. 6. When the switch network 44 is switched to the first "on" position, the voltage across the source coil 64 is positive as shown in FIG. 7 at reference number 66, thereby providing a positive polarity. When the switch network 44 is switched to the second "on" position, the voltage across the source coil 64 shifts and is negative as shown in FIG. 7 at reference number 68, thereby providing a negative polarity.

The switch network 44 (FIG. 6) alternates between the first and second "on" positions so as to alternate the voltage across the source coil 64 between the positive and negative polarities. When the switch network 44 is switched to the first "on" position, energy is drawn from the capacitor 42 toward the source coil 64. When the switch network 44 is switched to the second "on" position, energy is directed back to the capacitor 42 until the time when the current changes polarity and then energy is again drawn from the capacitor. When the switch network 44 is switched back to the first "on" position, then energy is again directed back to the capacitor 42 until the time when the current changes polarity again and then energy is again drawn from the capacitor. As a result, the switching network 44 is configured to alternately transfer stored energy from the energy storage device 42 to the source coil 64 and to transfer the storage energy from the source coil back to the energy storage device when alternately switching between the first and second "on" positions.

In one embodiment, the switch network 44 is configured so that the switches 62a–d (FIG. 6) are in the first "on" position for the same total time period for a particular pulse burst that they are in the second "on" position. Accordingly, the time period at the positive polarity is the same time period as the negative polarity for the voltage across the source coil 64. In the embodiment, when the switch network 44 is switched to the "off" position, the voltage across the source coil 64 is zero, as reflected at reference 70 in the voltage diagram. When the current through the source coil 64 (FIG. 6) is zero, the source coil provides no excitation signal 20 that would interfere with the marker signal 22 generated by the marker assembly 14 as discussed above.

Figure 8:
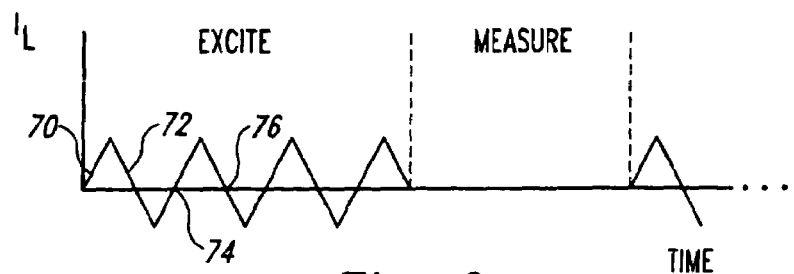
FIG. 8 is a schematic bipolar current diagram during the excitation "on" and excitation "off" phases over time of FIG. 7 for pulsed excitation and location of a marker assembly.

FIG. 8 is a schematic bipolar current diagram corresponding to the voltage diagram of FIG. 7. Referring to FIGS. 6, 7 and 8, when the switch network 44 (FIG. 6) is in the first "on" position corresponding so the voltage has a positive polarity 66 (FIG. 7), the current flow through the source coil 64 (FIG. 6) has a continually increasing current ramp 70 (FIG. 8) so as to generate the magnetic excitation field 20 with the positive polarity. When the switch network 44 (FIG. 6) is in the second "on" position corresponding to the negative polarity 68 (FIG. 7), the current flow has a continually decreasing current ramp 72 (FIG. 8). When the switch network 44 switches back to the first "on" position, the current flow switches back to an increasing current ramp 70. Accordingly, the current flow has a bipolar, generally non-sinusoidal triangular shaped waveform.

As seen in FIG. 8, when the current flow switches directions, for example from the decreasing current ramp 72 to the increasing current ramp 70, there is a point shown at 74 at which the current in the source coil is substantially at zero amps. Similarly, when the current flow has the decreasing current ramp 72, there is a point shown at 76 at which the current in the source coil 64 (FIG. 6) is at zero amps. The switch network 44 is configured to switch to the "off" position when the current flow through the source coil 64 is substantially at these zero points 74 and 76, and thus at zero amps. When the current in the source coil 64 approaches zero amps, the signal decay time for the pulsed excitation signal 20 approaches zero, such that the pulsed excitation signal is substantially instantaneously shut off so as to provide no interference with the marker signal 22 generated by the energized marker assembly 14.

In the embodiment wherein the excitation signal 20 is a CW signal, the switch network 44 continually switches between the first and second "on" positions during the time period when the marker signal is measured. In the pulsed excitation signal embodiment wherein the excitation signal is terminated when the switch network 44 is switched to the "off" position, the extent of signal decay over time of the source coil 64 current is a function of the resistance in the switch network as well as resistance and inductance in the source coil circuitry. In the illustrated embodiment, the switch network 44 and source coil 64 are configured such that when the switch network is switched to the "off" position, the stored energy in the source coil is minimized.

Figure 9:
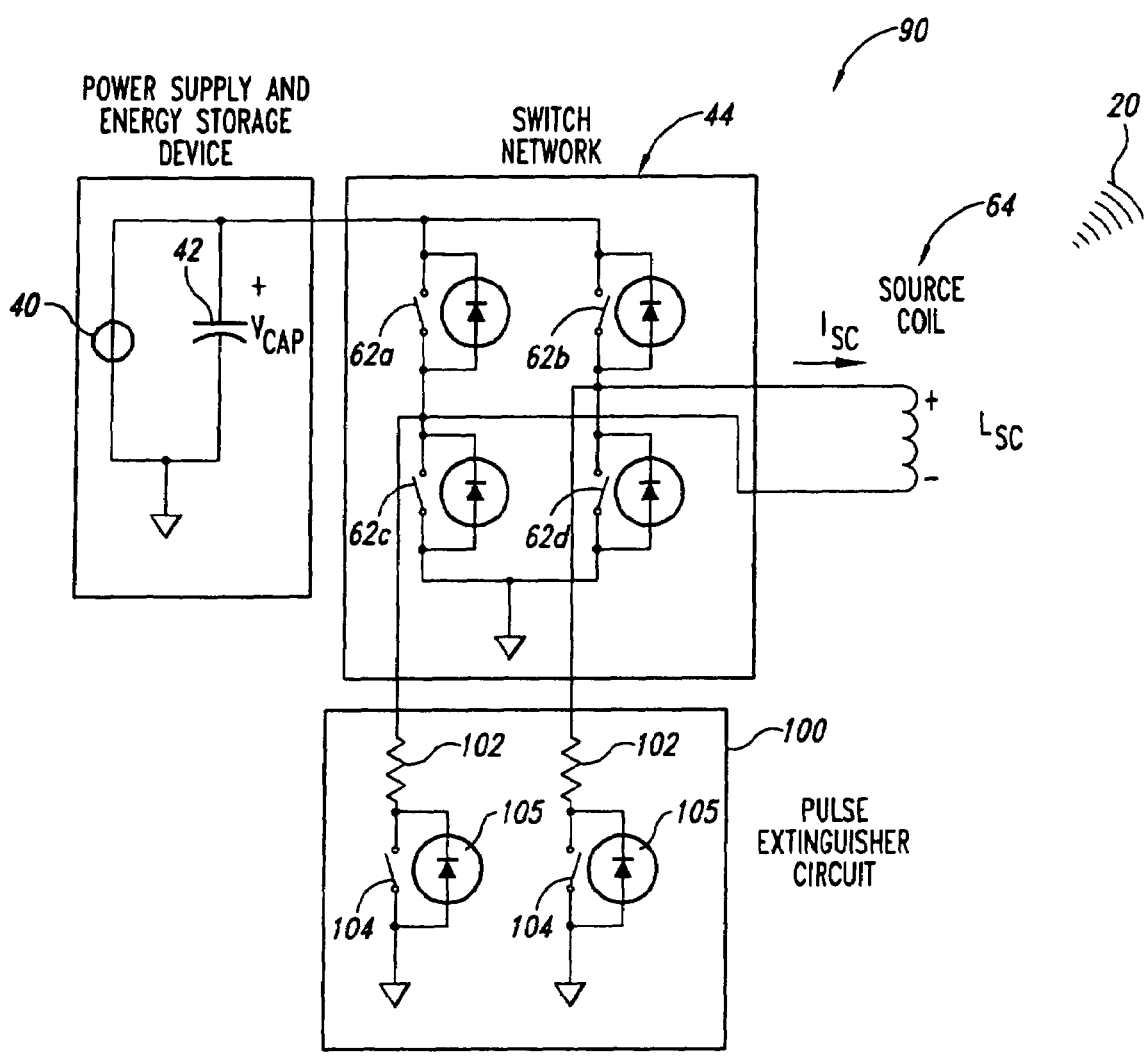
FIG. 9 is a schematic electrical diagram of an alternate embodiment of the system of FIG. 3, the system including a pulse extinguishing circuit.

FIG. 9 is a block diagram of a source signal generator 90 having a pulse extinguisher circuit 100 therein in accordance with an alternate embodiment. In this alternate embodiment, the source signal generator 90 includes the power supply 40 and the energy storage device 42 coupled to the switch network 44 similar to the embodiments discussed above. The switch network 44 is also coupled to the source coil 64. The switch network 44 is also connected to the pulse extinguisher circuit 100 in parallel with the source coil inductor, such that the pulse extinguisher circuit does not conduct current during pulse generation. The source signal generator 90 of this alternate embodiment provides the switch network 44 moveable between the first "on" position, the second "on" position as discussed above, and an "off" position where all of the switches, 62–62d, are opened. When the switch network 44 is switched to the "off" position, the pulse extinguisher circuit 100 switches 104 are closed to quickly dissipate the residual energy in the source coil 64 so as to limit the time that an excitation field continues to be generated after the switch network has been moved to the "off" position.

The pulse extinguisher circuit 100 is configured to include a pair of resistors 102 and switches 104 that can be activated to quickly dissipate the residual energy in the source coil when the circuit is closed and to interrupt the current flow through the extinguisher circuit when the switches 104 are open during excitation pulse generation. At the end of a pulse burst, the residual source coil current is conducted through one of the two switches 104, one of the two resistors 102 and an H-bridge protection diode 105, depending on the polarity of the residual current. Pairs of switches 104 and resistors 102 are provided so the residual current may be either of a positive or negative polarity. The time constant for de-energizing the source coil inductor is determined by the following equation:

$$\tau = L_{sc}/(R_L + R_{switch} + R_{protection\_diode} + R_{pulse\_extinguisher})$$

Where:
$L_{sc}$=Source coil inductance
$R_L$=Source coil resistance
$R_{switch}$=Switch "on" resistance
$R_{protection\_diode}$=Protection diode "on" resistance
$R_{pulse\_extinguisher}$=Pulse extinguisher resistor resistance The pulse extinguisher circuit's resistors 102 decrease the exponential decay time constant of residual current in the source coil by adding additional resistance to the source coil circuit only during turnoff time. As a result, the pulse extinguisher circuit 100 decreases the turnoff time of the source generator and does not decrease the overall energy efficiency or power dissipation of the source signal generator 90.

In the illustrated embodiment, the pulse extinguisher circuit 100 is configured so that no measurable or detectable excitation field remains after the switch network 44 has been moved to the "off" position within less than one cycle of the resonating marker assembly 14 (FIG. 1). Accordingly, the pulse extinguisher circuit 100 facilitates the termination of the pulsed excitation signal 20 so that the resonating marker assembly 14 can be easily detectable and located with the signal processing assembly 28 to accurately identify the three-dimensional location of the resonating marker assembly relative to the sensor array 16.

While the pulse extinguisher circuit 100 is defined in the illustrated embodiment as providing the resistors 102 and switches 104, with additional protection diodes 105, other pulse extinguisher circuits can be used so as to increase the resistance of the total source coil circuit when the switch network is in the "off" position. The alternate pulse extinguisher circuits should not increase system power dissipation and decrease energy efficiency by adding additional switch resistance during pulse delivery because of its presence.

Figure 10:
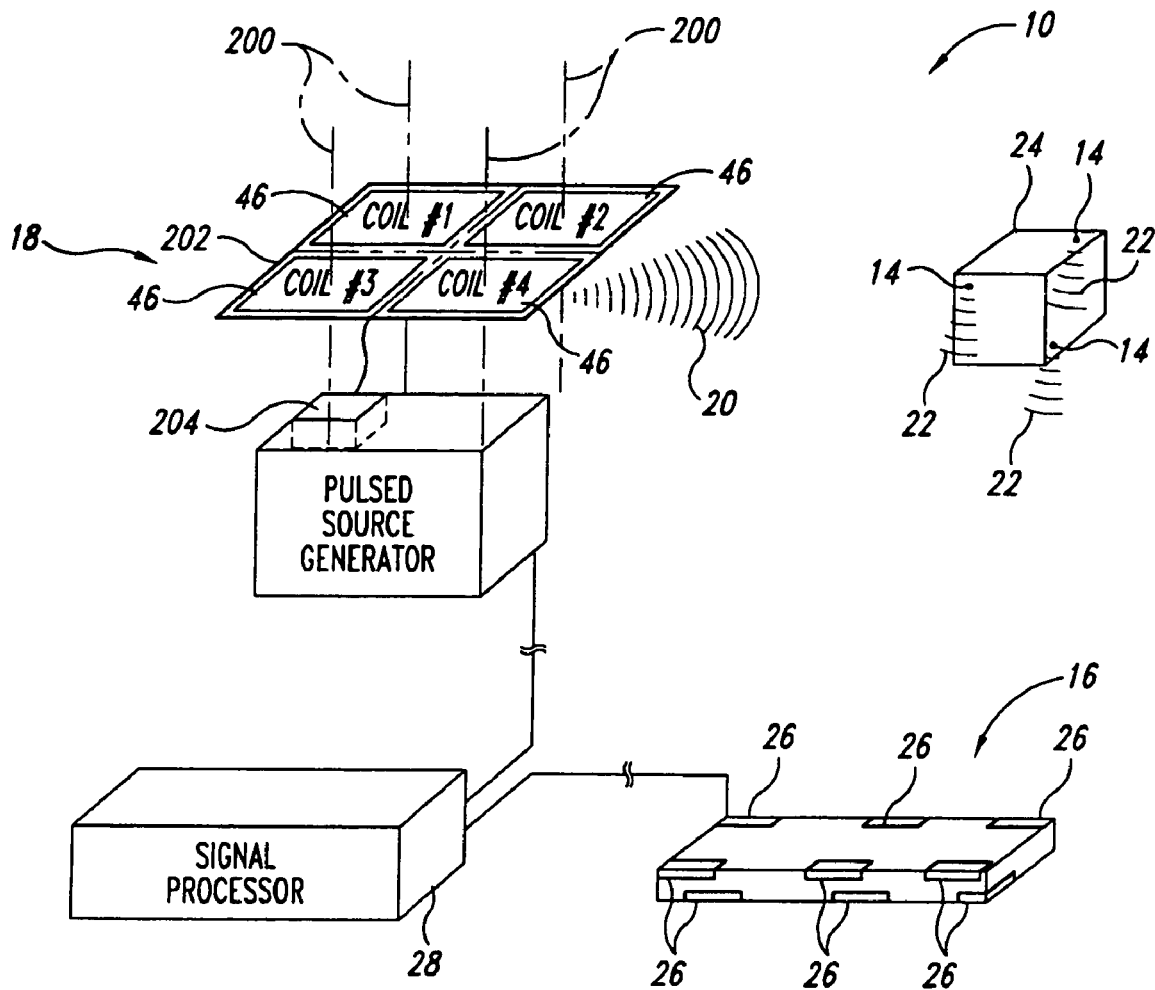
FIG. 10 is a schematic isometric view of an alternate embodiment of the system for energizing and locating leadless miniature markers.

FIG. 10 is an isometric view of an alternate embodiment of the system 10 for energizing and locating miniature leadless markers 14. In this alternate embodiment, the pulsed source generator 18 includes a plurality of excitation source coils 46 adjacent to each other and each independently coupled to the source generator. Each source coil 46 has primary coil axis 200 axially misaligned with the coil axis of the other source coils. In the illustrated embodiment, the plurality of source coils 46 include coils 1–4, and the four coils are all coplanar. Each of coils 1–4 has a square shape, and coils 1–4 are arranged so as to form a flat, substantially rectangular or square coil configuration. In alternate embodiments, other coil shapes and coil configuration shapes can be used with greater or fewer source coils 46. In one embodiment, coils 1–4 are embedded in a substantially planar substrate 202, such as a printed circuit board. In another embodiment, the coils 1–4 can be formed in separate substrates arranged so at least two of the source coils are substantially coplanar.

In one embodiment, the coil axes 200 of at least two source coils 46 (e.g., coils 1–4) are parallel, and in another embodiment, the coil axes of at least two source coils are nonconcentrically aligned with each other. In the illustrated embodiment, each of source coils 46 (e.g., coils 1–4) is adjacent to the other source coils while being electrically isolated from each other. Each of the source coils 46 is independently coupled to a source generator 204, such that a plurality of independently controlled, alternating electrical signals having adjustable phases can simultaneously be provided to the source coils. Each of coils 1–4 are configured to simultaneously receive one of the alternating electrical signals at a selected phase so as to generate a magnetic field around the respective source coil. As discussed in greater detail below, the magnetic fields from each of coils 1–4 combine to form a spatially adjustable excitation field that generates the source excitation signal at the selected frequency to energize the leadless markers 14.

Figure 11:
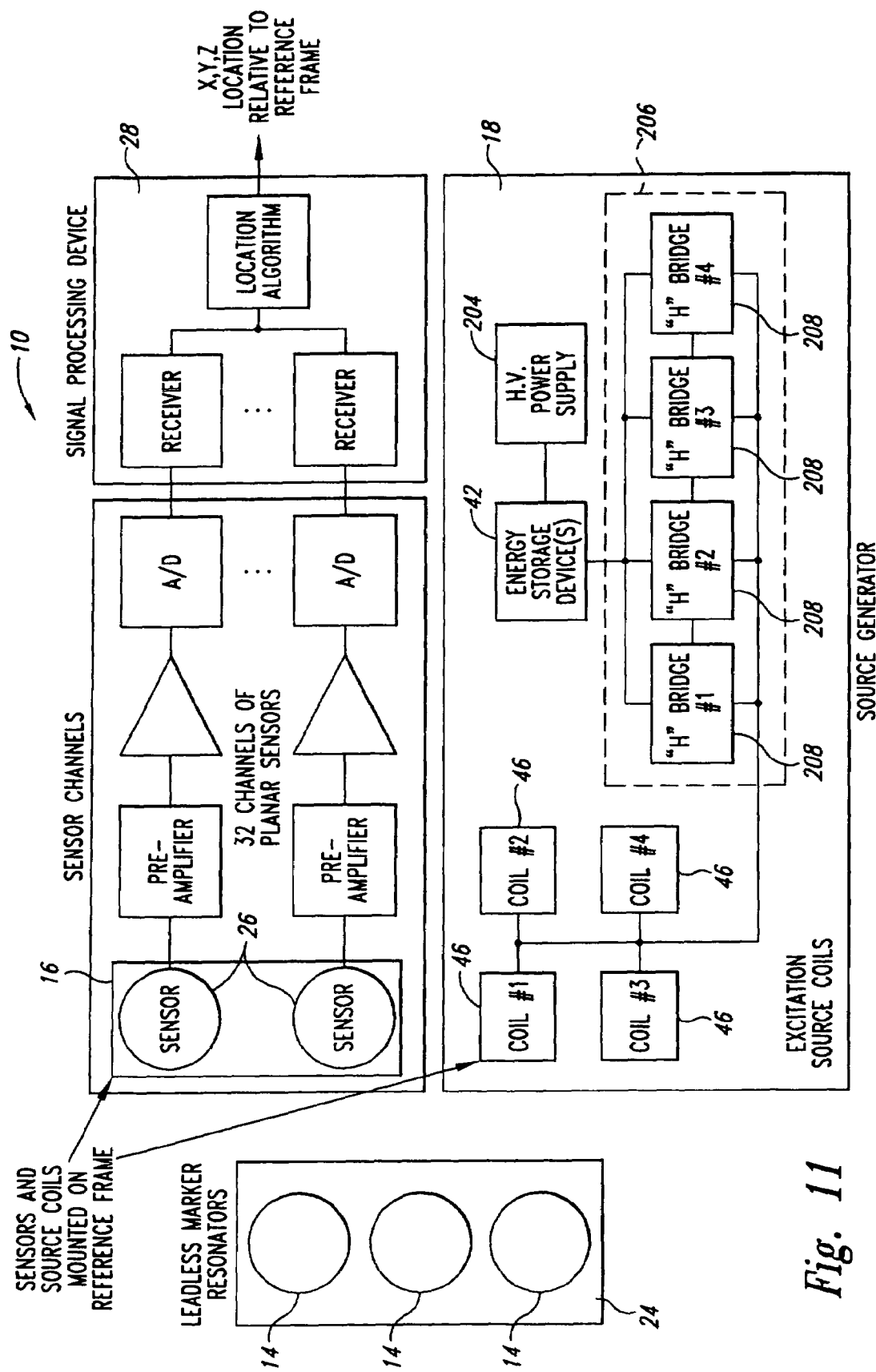
FIG. 11 is a schematic block diagram of the excitation system of FIG. 10 illustrating a source signal generator with four coplanar source coils.

FIG. 11 is a schematic block diagram of the system 10 in accordance with the alternate embodiment of FIG. 10. As seen in FIG. 11, the plurality of leadless miniature marker assemblies 14 on the target 24 are remote from the source generator 18 and from the sensors 16. In this alternate embodiment, the source generator 18 includes a switch network 206 with an H-bridge switch assembly 208 for each of coils 1–4. The switch network 206 is connected to the energy storage device 42, which is connected to the high voltage power supply 204. Each H-bridge 208 is configured to independently control the phase of the alternating electrical signal received by its respective source coil 46, thereby independently controlling the phase of the magnetic field generated by each of coils 1–4. For example, the H-bridges 208 can be configured so that the electrical signal for all of coils 1–4 are in phase or so the electrical signals for one or more of coils 1–4 are 180° out of phase. Furthermore, the H-bridges 208 can be configured so that the electrical signal for one or more of coils 1–4 are between 0 and 180° out of phase, thereby providing magnetic fields with different phases at the same point in time.

Figure 12:
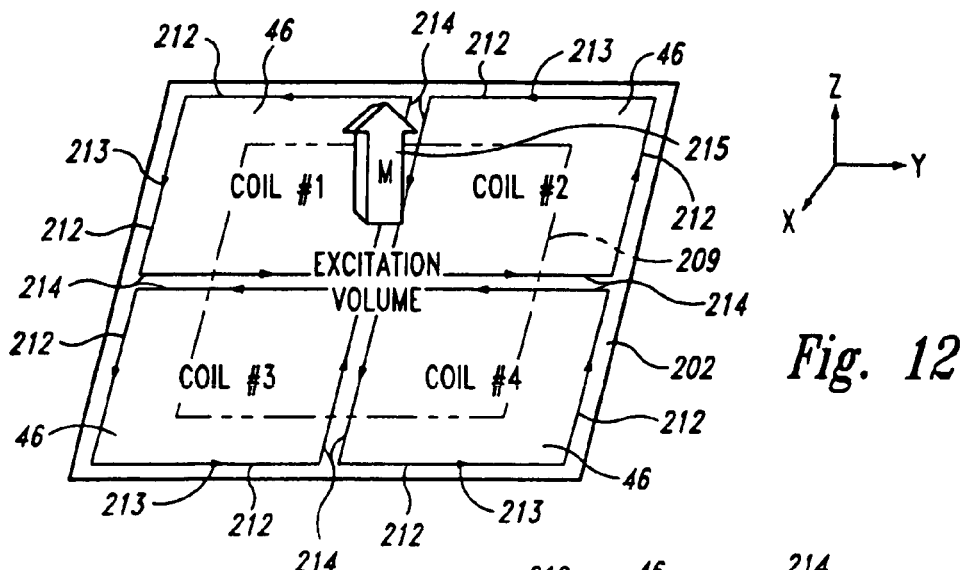
FIG. 12 is a schematic view of the coplanar source coils of FIG. 11 carrying electrical signals in a first combination of phases to generate a first excitation field.
Figure 13:
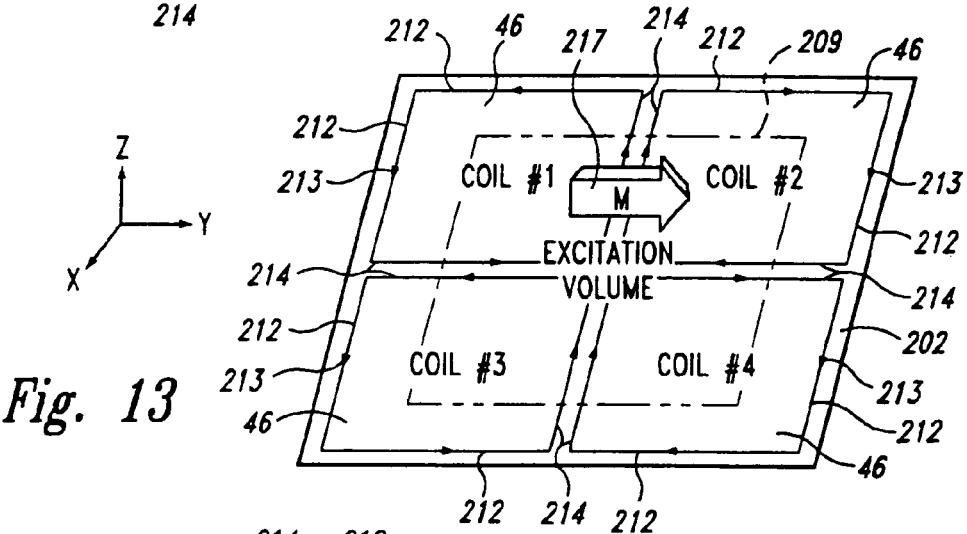
FIG. 13 is a schematic view of the coplanar source coils of FIG. 11 carrying the electrical signals in a second combination of phases to generate a second excitation field.
Figure 14:
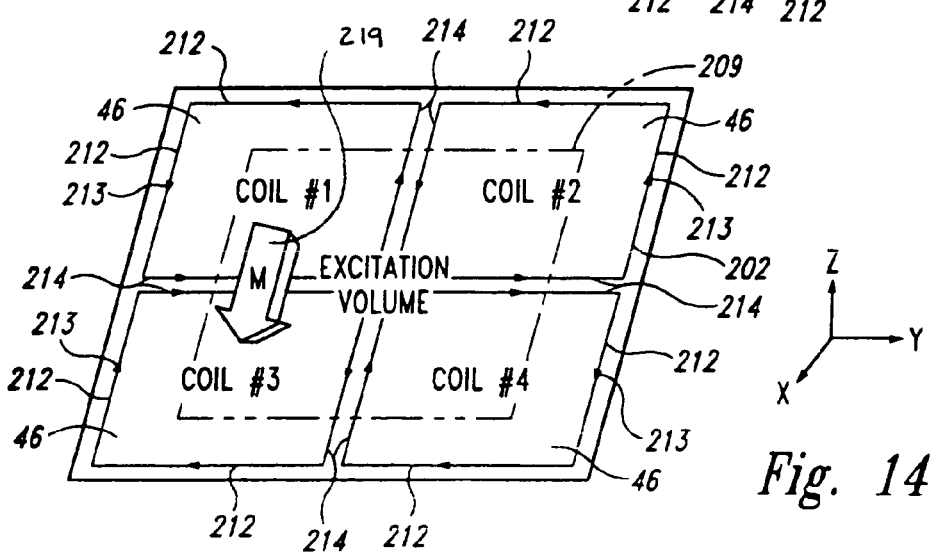
FIG. 14 is a schematic view of the coplanar source coils of FIG. 11 carrying the electrical signals in a third combination of phases to generate a third excitation field.

The selected magnetic fields from coils 1–4 combine together to form an adjustable, shaped excitation field that can have different three-dimensional shapes to excite the leadless markers 14 at any spatial orientation within an excitation volume 209 positioned adjacent to coils 1–4, as shown in FIGS. 12–14. In the illustrated embodiments, wherein coils 1–4 are shown generally horizontally oriented, the excitation volume 209 is positioned above an area approximately corresponding to the center of the array of source coils 46. The excitation volume 209 is the three-dimensional space adjacent to the source coils 46 in which the strength of the magnetic fields at the selected frequency is sufficient to fully energize the leadless markers 14 within that volume.

FIG. 12 is a schematic view of the coplanar source coils 46 (e.g., coils 1–4) of FIG. 11 with the alternating electrical signals provided to the source coils being in a first combination of phases to generate a first excitation field within the excitation volume 209 that provides significant magnetic field excitation about an axis in the Z-direction relative to the illustrated XYZ coordinate axis. Each of the coils 1–4 has four straight sides, two outer sides 212 and two inner sides 214. Each inner side 214 faces toward and is immediately adjacent to an inner side of another one of the source coils, and the two outer sides 212 face away from the other source coils.

In the embodiment of FIG. 12, coils 1–4 all receive an alternating electrical signal in the same phase at the same point in time. As a result, the electrical current is flowing in the same direction along coils 1–4. Accordingly, the direction of current flow along the inner sides 214 of one source coil (e.g., coil 1) is opposite to the current flow in the inner sides of the two adjacent source coils (e.g., coils 2 and 3). As a result, the magnetic fields generated along those adjacent inner sides 214 substantially cancel each other out, so the combined magnetic fields from coils 1–4 in this embodiment is effectively generated from the current flow around the outer sides 212 of coils 1–4. The resulting excitation field formed by the combination of the magnetic fields from coils 1–4 has a magnetic moment 215 substantially along the Z-axis within the excitation volume. This excitation field will be sufficient to energize the leadless markers 14 (FIG. 11) that are axially aligned along the Z-axis or that are positioned so the marker's longitudinal axis has an angular component along the Z-axis.

FIG. 13 is a schematic view of the coplanar source coils 46 (e.g., coils 1–4) of FIG. 11 with the alternating electrical signals provided to the source coils in a second combination of phases to generate a second excitation field with a different spatial orientation. In this embodiment, coils 1 and 3 are in phase, and coils 2 and 4 are in phase, but coils 1 and 3 are 180 degrees out of phase with coils 2 and 4. The direction of current flow around each coil 46 is shown by the direction arrows 213. As a result, the magnetic fields from coils 1–4 combine to generate an excitation field 217 generally in the Y direction within the excitation volume 209 that provides significant magnetic field excitation. Accordingly, this excitation field is sufficient to energize the leadless markers 14 that are axially aligned along the Y-axis or that are positioned so the marker's longitudinal axis has an angular component along the Y-axis.

FIG. 14 is a schematic view of the coplanar source coils 46 (e.g., coils 1–4) of FIG. 11 with the alternating electrical signals being provided to coils 1–4 in a third combination of phases to generate a third excitation field with a different spatial orientation. In this embodiment, coils 1 and 2 are in phase, and coils 3 and 4 are in phase, but coils 1 and 2 are 180 degrees out of phase with coils 3 and 4. Accordingly, the magnetic fields from coils 1–4 combine to generate an excitation field 219 in the excitation volume 209 generally along the X-axis within the excitation volume. Accordingly, this excitation field is sufficient to energize the leadless markers 14 that are axially aligned along X-axis or that are positioned so the marker's longitudinal axis has an angular component along the X-axis.

Figure 15:
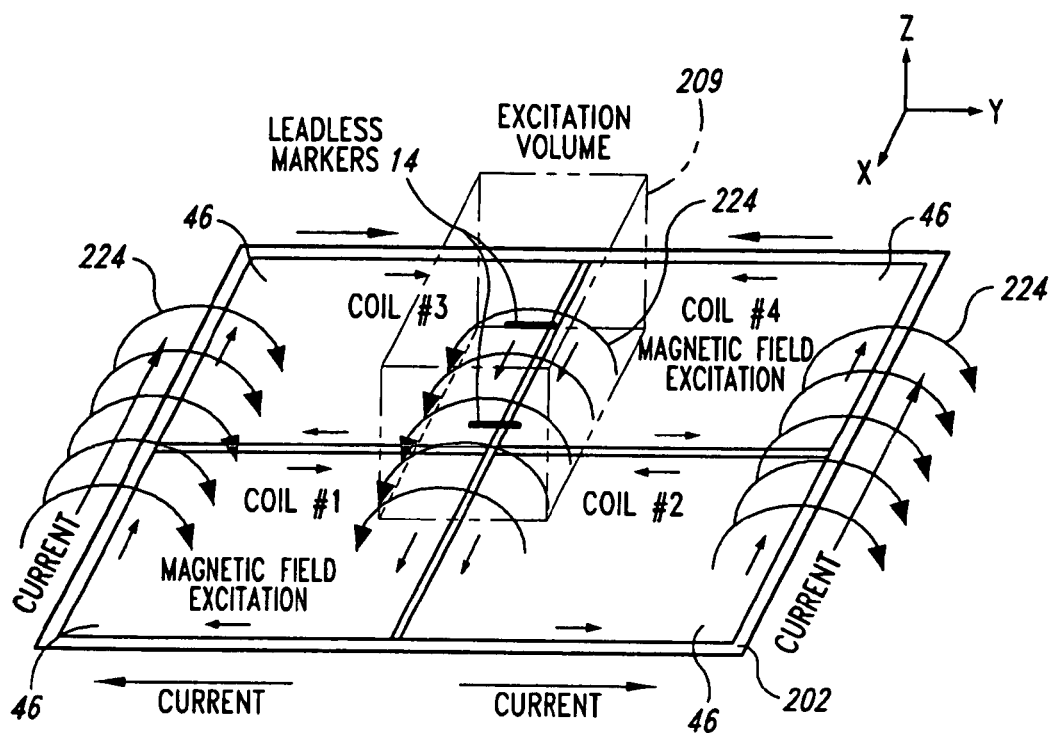
FIG. 15 is a schematic view of the coplanar source coils of FIG. 11 illustrating one magnetic excitation field from the current flows along the coils for excitation of leadless markers in a first spatial orientation.

FIG. 15 is a schematic view of the coplanar source coils 46 of FIG. 10 illustrating the magnetic excitation field and the current flow to generate the excitation field 224 for excitation of the leadless markers 14 in a first spatial orientation. In this illustrated embodiment, two leadless markers 14 are oriented within the excitation volume 209 spaced above coils 1–4 such that the longitudinal axis of each of the leadless markers is substantially parallel to the planar coils and aligned with the Y-axis within the excitation volume. The switch network 206 (FIG. 11) is configured so the phase of the alternating electrical signals provided to coils 1–4 are similar to the configuration of FIG. 13 so as to generate an excitation field represented by field lines 224 within the excitation volume 209.

Figure 16:
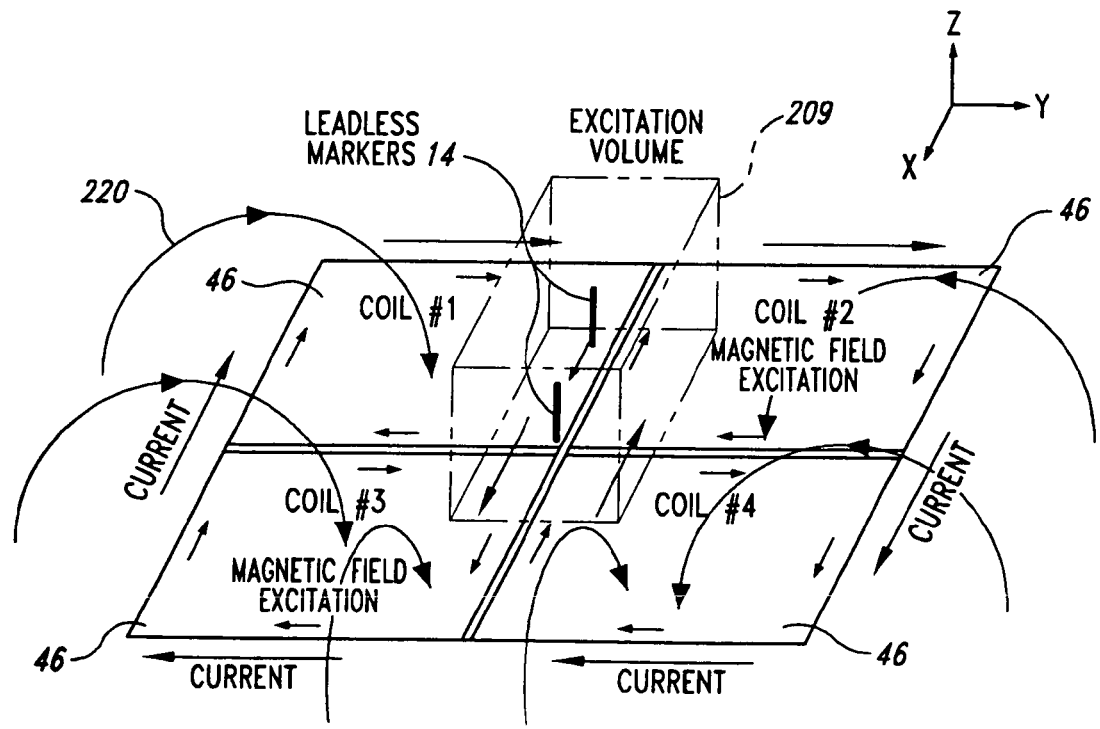
FIG. 16 is a schematic view of the coplanar source coils of FIG. 11 illustrating another magnetic excitation field from the current flows along the coils for excitation of leadless markers in a second spatial orientation.

The excitation field 20 (FIG. 10) is spatially adjustable to create a different excitation field by adjusting the switch network 206 (FIG. 10) to change the phase of the electrical signals in one or more of coils 1–4, so as to energize any leadless markers 14 at different spatial orientations. As an example, FIG. 16 is a schematic view of the coplanar source coils alternating electrical signals with phases different from the embodiment of FIG. 15 and the resulting excitation field 220 for excitation of the leadless markers 14 within the excitation volume 209. In this embodiment, the current flow through coils 1–4 is similar to that as shown in FIG. 12, such that the excitation field 220 within the excitation volume 209 is at a spatial orientation so as to excite the illustrated leadless markers 14 oriented normal to the coils 1–4.

The spatial configuration of the excitation field 220 in the excitation volume 209 can be quickly adjusted by adjusting the switch network 206 (FIG. 10) and changing the phases of the electrical signals independently provided to the coplanar coils 1–4. As a result, the overall magnetic excitation field can be changed to be substantially oriented in either the X, Y or Z directions within the excitation volume 209. This adjustment of the spatial orientation of the excitation field 220 effectively avoids any blind spots in the excitation volume 209. Therefore, the remote, miniature leadless markers 14 within the excitation volume 209 can be energized via the coplanar source coils 46 regardless of the spatial orientations of the leadless markers.

In one embodiment, the source generator 18 is coupled to the sensor array 16 so that the switch network 206 (FIG. 10) adjusts orientation of the pulsed generation of the excitation field 220 along the X, Y, or Z axis, depending upon the strength of the signal received by the sensor array. If an insufficient marker signal is received from the sensor array 16, the switch network 206 can be automatically adjusted to change the spatial orientation of the excitation field 220 during a subsequent pulsing of the source coils 46 to generate the excitation field oriented along a different axis or oriented between the axes. The switch network 206 can be adjusted until the sensor array 16 receives a sufficient signal, thereby ensuring sufficient excitation of the leadless markers 14 within the excitation volume 209.

Although specific embodiments of, and examples for, the present invention are described herein for illustrative purposes, various equivalent modifications can be made without departing from the spirit and scope of the invention, as will be recognized by those skilled in the relevant art. The teachings provided herein of the present invention can be applied to systems for excitation of leadless miniature markers, not necessarily the exemplary system generally described above.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A system for generating a spatially adjustable excitation field, comprising:
   a source generator that generates a plurality of alternating electrical signals each having an independently adjustable phase; and
   a plurality of excitation coils being configured to simultaneously receive the alternating electrical signals at a selected phase to generate magnetic fields, wherein the magnetic fields combine to form a spatially adjustable excitation field for excitation of a leadless resonating marker assembly within the spatially adjustable excitation field.

2. The system of claim 1 wherein the excitation coils are co-planar.

3. The system of claim 1 wherein the coil axes of at least two excitation coils are parallel.

4. The system of claim 1 wherein the coil axes of at least two excitation coils are non-concentric.

5. The system of claim 1 wherein the plurality of excitation coils includes four co-planar excitation coils.

6. The system of claim 1 wherein the alternating electrical signal for each coil is non-sinusoidal.

7. The system of claim 1 wherein the plurality of excitation coils include four side-by-side excitation coils each having straight sides parallel to at least one side of two other of the excitation coils.

8. The system of claim 1 wherein the plurality of excitation coils includes at least two co-planar excitation coils.

9. The system of claim 1 wherein the excitation coils are mounted on a substantially planar substrate.

10. The system of claim 1 wherein the excitation coils include first and second excitation coils, the first excitation coil being configured to receive an alternating electrical signal with a first selected phase to generate a first magnetic field, and the second excitation coil being configured to receive an alternating electrical signal with the first selected phase to generate a second magnetic field to combine with the first magnetic field to generate a first shaped excitation field, and the second excitation coil being configured to receive an alternating electrical signal with a second selected phase substantially different from the first selected phase to form a third magnetic field that combines with the first magnetic field to form a second excitation field with different spatial characteristics than the first excitation field.

11. A method of exciting a leadless marker assembly, comprising:
directing alternating electrical signals that have independently adjustable phase through a plurality of excitation coils;
generating a plurality of magnetic fields from the plurality of excitation coils;
combining the magnetic fields to form a spatially adjustable excitation field; and
energizing a leadless resonating marker assembly within the spatially adjustable excitation field.

12. The method of claim 11 wherein the alternating electrical signals are a non-sinusoidal waveform having both a positive and negative polarity.

13. The method of claim 12, further comprising:
measuring a marker signal after the alternating electrical signals have been terminated.

14. The method of claim 11 further comprising:
terminating the alternating electrical signals while the resonating marker assembly is energized; and
receiving a marker signal at a plurality of sensors while the alternating electrical signals are terminated.

15. The method of claim 14, further comprising:
using a pulse extinguisher circuit coupled to a switching network and configured to reduce the time constant of a residual source signal decay.

16. The method of claim 14 wherein the marker signal has a resonant frequency, and terminating the alternating electrical signals include turning off electrical voltage at a selected time so that substantially no electrical current reaches the excitation coils within one cycle or less of the marker signal at the resonant frequency.

17. The method of claim 14, further comprising:
adjusting a pulse waveform of the magnetic fields to excite markers of different resonant frequencies.

18. A system for generating a pulsed excitation field for excitation of a lead less marker assembly, comprising:
a high voltage capacitor;
a source coil having a programmable frequency configured to deliver a pulsed magnetic excitation signal to the leadless marker assembly; and
a switching network coupled to the high voltage capacitor and the source coil, wherein the switching network is configured to redirect a continuous flow of energy from the high voltage capacitor to the source coil and from the source coil back to the high voltage capacitor.

19. The system of claim 18 wherein the pulsed magnetic excitation field source signal has a generally triangular-shaped bipolar waveform having a positive and negative polarity.

20. The system of claim 18 wherein the pulsed magnetic excitation signal has a generally triangular-shaped unipolar waveform having only a single polarity.

21. The system of claim 18 wherein the pulsed magnetic excitation signal has a non-sinusoidal waveform having a positive and negative polarity.

22. The system of claim 18 wherein the switching network includes at least two switches configured to switch voltage across the source coil between a positive voltage polarity and a negative voltage polarity.

23. The system of claim 18 wherein the switching network is configured to move to the off position when electrical current in the switching network is at approximately zero amps.

24. The system of claim 18, further comprising a leadless resonating marker remote from the source coil, and being excitable by the pulsed magnetic excitation signal to generate a marker resonant signal with selected frequency components.

25. The system of claim 18 wherein the switching network is configured to substantially prevent the source coil from generating any excitation signal within one cycle or less of the marker resonant signal.

26. The system of claim 25, further comprising a plurality of sensors configured to measure signals from the leadless marker assembly upon excitation by the pulsed magnetic excitation signal.

27. The system of claim 18, further comprising a pulse extinguisher circuit coupled to the switching network and configured to reduce the time constant of the residual source signal decay of the pulsed magnetic excitation signal.

28. The system of claim 18 wherein the pulsed magnetic excitation signal is a programmable pulse burst duration magnetic excitation signal.

29. The system of claim 18 wherein the pulsed magnetic excitation signal is a programmable pulse repetition frequency magnetic excitation signal.

30. The system of claim 18 wherein the switching network and the source coil are a first switch network and first source coil, respectively, that generate a first source signal in a first spatial orientation, and further comprising a second switch network and a second source coil that generate a second source signal in a second spatial orientation different than the first spatial orientation.

31. The system of claim 30, further including a third switch network and third source coil that generate a third source signal in a third spatial orientation different than the first and second spatial orientations.

* * * * *